United States Patent
Kashiwase

(10) Patent No.: US 10,813,557 B2
(45) Date of Patent: Oct. 27, 2020

(54) MEASUREMENT APPARATUS, MEASUREMENT INSTRUMENT, MEASUREMENT SYSTEM, SERVER, ANALYSIS METHOD, STORAGE MEDIUM, AND DATA STRUCTURE

(71) Applicant: KYOCERA Corporation, Kyoto-shi, Kyoto (JP)

(72) Inventor: Susumu Kashiwase, Machida (JP)

(73) Assignee: KYOCERA CORPORATION, Kyoto (JP)

( * ) Notice: Subject to any disclaimer, the term of this patent is extended or adjusted under 35 U.S.C. 154(b) by 338 days.

(21) Appl. No.: 15/986,041

(22) Filed: May 22, 2018

(65) Prior Publication Data

US 2018/0338687 A1    Nov. 29, 2018

(30) Foreign Application Priority Data

May 26, 2017  (JP) ................................. 2017-105024

(51) Int. Cl.
*A61B 5/01*    (2006.01)
*A61B 5/00*    (2006.01)

(52) U.S. Cl.
CPC .............. *A61B 5/01* (2013.01); *A61B 5/0097* (2013.01); *A61B 5/6817* (2013.01); *A61B 2562/0271* (2013.01)

(58) Field of Classification Search
CPC .......... A61B 5/01; A61B 5/68147; A61B 5/02; A61B 5/0097; A61B 2563/0271
See application file for complete search history.

(56) References Cited

U.S. PATENT DOCUMENTS

| | | | |
|---|---|---|---|
| 10,341,757 B2* | 7/2019 | Fujimoto | ............. H04R 1/2857 |
| 2013/0218022 A1* | 8/2013 | Larsen | .................... A61B 5/01 |
| | | | 600/474 |
| 2015/0092952 A1 | 4/2015 | Sudo et al. | |
| 2018/0214041 A1* | 8/2018 | Hidaka | ............. A61B 5/02438 |
| 2019/0212198 A1* | 7/2019 | Marsh | ................... G01J 5/0011 |

FOREIGN PATENT DOCUMENTS

JP    2015-70514 A    4/2015

* cited by examiner

*Primary Examiner* — Catherine T. Rastovski
(74) *Attorney, Agent, or Firm* — Hauptman Ham, LLP

(57) ABSTRACT

Provided are a measurement apparatus, a measurement instrument, a measurement system, a server, an analysis method, a storage medium and a data structure that easily enable good acoustic characteristics while improving the accuracy of body temperature detection. The measurement apparatus includes a metal tube having a first end and a second end; a measurement unit which is arranged at the first end 13*a* side of the metal tube and is capable of measuring electromagnetic radiation incident from the second end of the metal tube; a sound output unit configured to output sound; and a first path and a second path to the first end of the metal tube for sound outputted from the sound output unit, wherein the first path and the second path have different lengths.

16 Claims, 18 Drawing Sheets

FIG. 6

| | | |
|---|---|---|
| 600 — Health information | Body temperature higher than average. | — 601 |
| | Body temperature lower than average. | — 603 |
| 630 — Music information | Music 1 | — 631 |
| | Music 2 | — 633 |
| | Music 3 | — 635 |
| | Music 4 | — 637 |
| | Music 5 | — 639 |
| | Music 6 | — 641 |
| 650 — Environment information | Temperature to rise. | — 651 |
| | Temperature to fall. | — 653 |
| | Rain. | — 655 |

FIG. 10A  D10

| • ID | • Measurement date and time | Body temperature | Weather | Atmospheric temperature |
|---|---|---|---|---|
| 3001 | 3003 | 3005 | 3007 | 3009 |

FIG. 10B  D20

| • ID | Age | Gender |
|---|---|---|
| 3001 | 3011 | 3013 |

FIG. 10C  D30

| • Measurement date and time | • Weather | • Atmospheric temperature | • Age | • Gender | Average body temperature |
|---|---|---|---|---|---|
| 3003 | 3007 | 3009 | 3011 | 3013 | 3015 |

FIG. 10D  D40

| • ID | • Measurement date and time | • Weather | • Atmospheric temperature | Individual average body temperature |
|---|---|---|---|---|
| 3001 | 3003 | 3007 | 3009 | 3017 |

MEASUREMENT APPARATUS, MEASUREMENT INSTRUMENT, MEASUREMENT SYSTEM, SERVER, ANALYSIS METHOD, STORAGE MEDIUM, AND DATA STRUCTURE

CROSS-REFERENCE TO RELATED APPLICATION

The present application claims priority to and the benefit of Japanese Patent Application No. 2017-105024 filed May 26, 2017, the entire contents of which are incorporated herein by reference.

TECHNICAL FIELD

The present disclosure relates to a measurement apparatus, a measurement instrument, a measurement system, a server, an analysis method, a storage medium, and a data structure.

BACKGROUND

Earphones capable of measuring body temperature are known. For example, a canal type earphone provided with a body temperature sensor is known.

SUMMARY

A measurement apparatus according to a first aspect of the present disclosure includes a metal tube, a measurement unit, and a sound output unit. The metal tube has a first end and a second end. The measurement unit is arranged at a first end side of the metal tube and is capable of measuring electromagnetic radiation incident from the second end of the metal tube. The sound output unit is configured to output sound. The measurement apparatus includes a first path and a second path to the first end of the metal tube for sound outputted from the sound output unit. The first path and the second path have different lengths.

A measurement instrument according to a second aspect of the present disclosure includes a first measurement unit configured as a blood flow measurement apparatus capable of measuring blood flow, and the measurement apparatus according to the first aspect.

A measurement system according to a third aspect of the present disclosure includes the measurement apparatus according to the first aspect; a control apparatus for controlling operation of the measurement apparatus; and a server connected to the measurement apparatus via a network, wherein the server is configured to receive information on electromagnetic radiation measured by the measurement apparatus, analyze the received information based on information stored in a memory, and transmit the analyzed information to the control apparatus.

A server according to a fourth aspect of the present disclosure is connected to a control apparatus for controlling operation of the measurement apparatus according to the first aspect via a network; wherein the server is configured to receive information on electromagnetic radiation measured by the measurement apparatus, analyze the received information based on information stored in a memory, and transmit analysis information indicating a result of the analysis to the control apparatus.

An analysis method according to a fifth aspect of the present disclosure is to be performed by a server connected to a control apparatus configured to control operation of the measurement apparatus according to the first aspect via a network; wherein the analysis method includes receiving information on electromagnetic radiation measured by the measurement apparatus, analyzing the received information based on information stored in a memory, and transmitting analysis information indicating a result of the analysis to the control apparatus.

A non-transitory computer readable storage medium storing an analysis program according to a sixth aspect of the present disclosure which, when executed by a computer, causes the computer to receive information on electromagnetic radiation measured by the measurement apparatus according to the first aspect, analyze the received information based on information stored in a memory, and transmit analysis information indicating a result of the analysis to a control apparatus.

A data structure according to a seventh aspect of the present disclosure is configured for use in a computer, including information on electromagnetic radiation measured by a measurement apparatus according to the first aspect, a user ID of a user of the measurement apparatus, an average body temperature of a group to which the user belongs, and an individual average body temperature of the user; wherein the computer is used to determine whether information on electromagnetic radiation measured by the measurement apparatus is abnormal based on at least one of the average body temperature and the individual average body temperature.

BRIEF DESCRIPTION OF THE DRAWINGS

In the accompanying drawings:

FIG. 6 is a conceptual diagram of sound data to be stored in a memory of the control apparatus;

FIGS. 10A, 10B, 10C, and 10D are configuration diagrams illustrating an example of data to be stored in the server in FIG. 7;

DETAILED DESCRIPTION

For conventionally known earphones capable of measuring body temperature, it is difficult to obtain good acoustic characteristics while improving the accuracy of body temperature detection.

For example, in a conventionally known earphone, a body temperature sensor is provided substantially in the center of an opening of an acoustic cylinder configured to face an eardrum. In this case, body temperature measured by the body temperature sensor may have absorbed infrared energy radiated from, for example, the wall surface of an ear canal or the like, other than the eardrum. The wall surface of the ear canal or the like, however, is more easily affected by outside air than the eardrum. Thus, when a body temperature sensor measures body temperature based on infrared energy radiated from the wall surface of an ear canal or the like, it is difficult to accurately measure the body temperature of a subject.

It would be helpful to provide a measurement apparatus, a measurement instrument, a measurement system, a server, an analysis method, a storage medium, and a data structure that easily enable good acoustic characteristics while improving the accuracy of body temperature detection.

A plurality of embodiments according to the present disclosure will be described with reference to the accompanying drawings.

Embodiment 1

Figure 1:
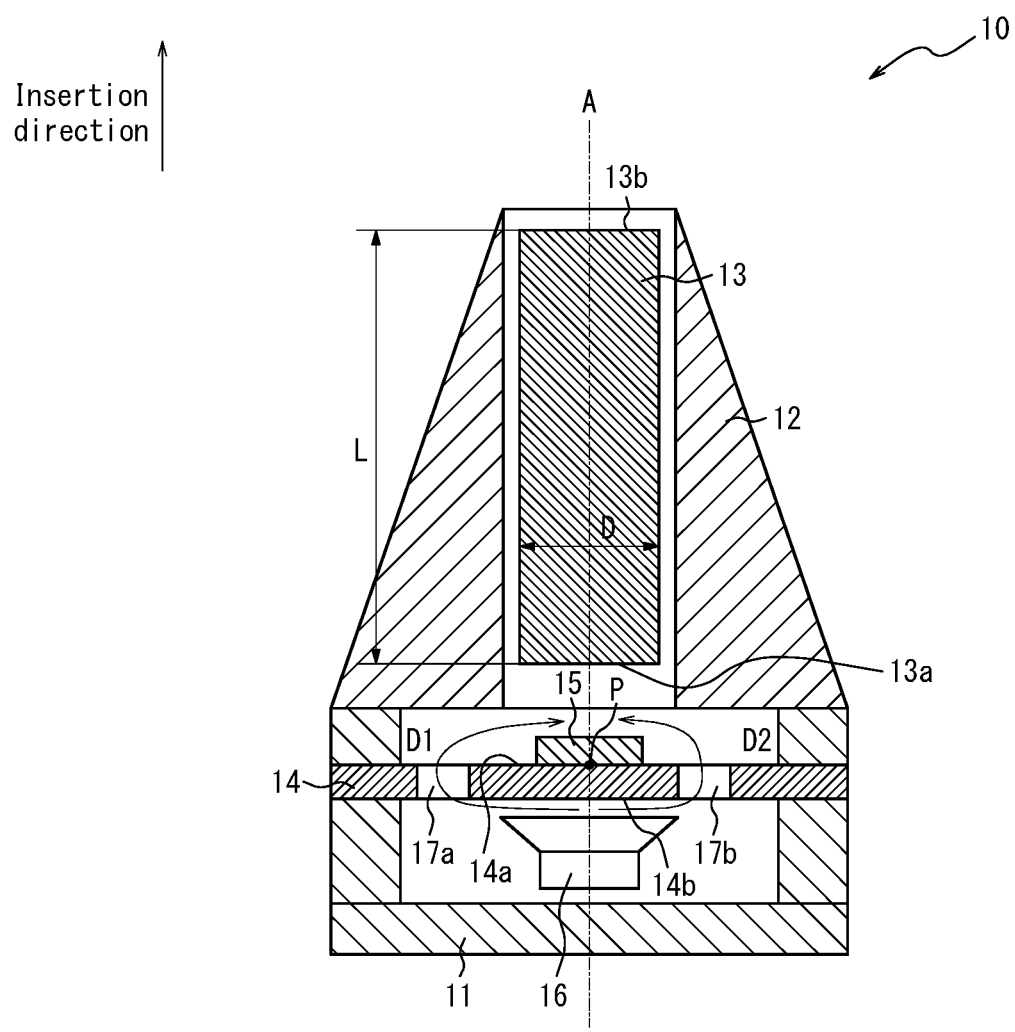
FIG. 1 is a schematic diagram illustrating the internal structure of a measurement apparatus according to Embodiment 1.

FIG. 1 is a schematic diagram illustrating the internal structure of a measurement apparatus 10 according to Embodiment 1. The measurement apparatus 10 is an apparatus to be inserted into a subject's ear canal for use. The outer shape of the measurement apparatus 10 may be a canal type earphone. The measurement apparatus 10, when inserted in the subject's ear, is capable of measuring biological information. The biological information may be information that can be acquired by a biological sensor described later. Hereinafter, the biological information will be described as the subject's body temperature. The measurement apparatus 10 also functions as an earphone. Thus, in a state in which the measurement apparatus 10 is inserted in the subject's ear (hereinafter, also referred to as "wearing state"), the subject can listen to sound outputted from the measurement apparatus 10 while measuring body temperature with the measurement apparatus 10.

As schematically illustrated in FIG. 1 as an example, the measurement apparatus 10 includes a holder 11, an earpiece 12, a metal tube 13, a substrate 14, a measurement unit 15, and a sound output unit 16.

The holder 11 holds and protects various mechanisms included in the measurement apparatus 10. The holder 11 may be formed from a resin or the like. When the measurement apparatus 10 is connected to an external device configured to control sound output in a wired manner, a cable for connection with the external device may extend from the holder 11. The holder 11 and the earpiece 12 are coupled to form the outer shape of the measurement apparatus 10. The holder 11 is formed so as to surround the substrate 14.

The earpiece 12 is to be inserted into the subject's ear canal along the insertion direction indicated by the arrow in FIG. 1. That is, the subject can wear the measurement apparatus 10 by inserting the earpiece 12 into an ear canal. The earpiece 12 may be formed from a flexible member such as silicon or the like. Because of the flexibility of the earpiece 12, the subject can easily insert the measurement apparatus 10 into an ear canal and maintain the wearing state of the measurement apparatus 10. The earpiece 12 may, for example, be rotationally symmetrical with respect to the virtual axis A illustrated in FIG. 1. The direction of the axis A may be aligned with the insertion direction indicated by the arrow. As viewed from the insertion direction, a cylindrical space is provided in the center of the earpiece 12. The metal tube 13 is held in this space.

The metal tube 13 is a cylindrical metallic tube which is rotationally symmetrical with respect to the axis A. In the wearing state of the measurement apparatus 10, the metal tube 13 functions as a waveguide for electromagnetic radiation radiated from the subject. The electromagnetic radiation may, for example, be infrared radiation. Infrared radiation, for example, is electromagnetic radiation with a wavelength in the range of 1 to 20 μm. Hereinafter, the electromagnetic radiation will be described as infrared radiation.

In order to reduce the emissivity of the inner surface of the metal tube 13, gold plating may be applied thereto. The inner surface of the metal tube 13 may be formed from a material with low emissivity to infrared radiation, such as silver. The length L of the metal tube 13 is longer than the diameter D of the metal tube 13 by a predetermined length or more. For example, the length L may be three times the diameter D or more. The metal tube 13 has a first end 13a and a second end 13b. In the measurement apparatus 10, the metal tube 13 is arranged such that the first end 13a is located at the holder 11 side, and the second end 13b is located at the opening side of the measurement apparatus 10. That is, the second end 13b faces the incident direction of infrared radiation in the wearing state of the measurement apparatus 10.

The substrate 14, for example, as illustrated in FIG. 1, is held in the holder 11 and is orthogonal to the axis A. The substrate 14 has a first surface 14a facing the metal tube 13 and a second surface 14b on the other side. The substrate 14 has at least two openings. In the present embodiment, the substrate 14 will be described as having two openings hereinafter, namely, a first opening 17a and a second opening 17b. The first opening 17a and the second opening 17b are provided on the substrate 14 at positions with different distances from a point P at which the substrate 14 and the axis A intersect.

The shape of the openings 17a and 17b may be circular, oval, polygonal, or any combination thereof. In the present embodiment, the shape of the openings 17a and 17b are circular.

The measurement unit 15 is configured to acquire infrared radiation radiated from the subject, and output a photoelectric conversion signal for the acquired infrared radiation as biological information related to body temperature to a control apparatus 500 described later. Then, the control apparatus 500 measures the subject's body temperature based on the photoelectric conversion signal outputted from the measurement unit 15. The measurement unit 15 is arranged on the first surface 14a, and may be disposed at the position of the intersection point P.

The sound output unit 16 is configured to output sound based on an inputted sound signal. Here, the sound signal, for example, is inputted to the sound output unit 16 from an external device in a wired manner, a wireless manner, or the like. The sound output unit 16 may be constituted, for example, by a dynamic speaker. The sound output unit 16 is arranged at the second surface 14b side of the substrate 14, for example, in a space provided in the holder 11. The sound output unit 16 may be provided on the axis A. Sound outputted from the sound output unit 16 is configured to pass through the first opening 17a, the second opening 17b and the metal tube 13, and then be outputted to the outside of the measurement apparatus 10 from the second end 13b. In the wearing state of the measurement apparatus 10, the subject can listen to sound outputted in this way.

In the present embodiment, sound outputted from the sound output unit 16 is configured to reach the first end 13a of the metal tube 13 through two paths, namely, a first path and a second path. The first path is a path from the sound output unit 16 to the first end 13a via the first opening 17a, and the second path is a path from the sound output unit 16 to the first end 13a via the second opening 17b.

Here, measurement of body temperature by the measurement apparatus 10 will be described in detail. In the measurement apparatus 10, the measurement unit 15 is configured to acquire infrared radiation radiated from the subject. Infrared radiation radiated from a subject is configured to enter the metal tube 13 from the second end 13b and then be received by the measurement unit 15. In the present embodiment, the length L of the metal tube 13 is longer than the diameter D thereof by a predetermined amount or more; and the measurement unit 15 is arranged at the inner side of the metal tube 13, namely, the first end 13a side.

It is assumed that the measurement unit 15 is able to receive infrared radiation radiated from the wall surface of an ear canal, when the length L of the metal tube 13 is not longer than the diameter D thereof by the predetermined amount, or when the measurement unit 15 is arranged at the second end 13b side of the metal tube 13. The wall surface of an ear canal, however, is easily affected by outside air. Thus, infrared radiation received by the measurement unit 15 in this case is not necessarily based on the actual body temperature of the subject, and may be based on a body temperature affected by outside air temperature. Consequently, it would be difficult to accurately measure the body temperature of a subject.

On the contrary, according to the measurement apparatus 10 of the present embodiment, the directivity of infrared radiation to be received by the measurement unit 15 can be increased, compared to the case that the length L of the metal tube 13 is not longer than the diameter D thereof by the predetermined amount, or the case that the measurement unit 15 is arranged at the second end 13b side of the metal tube 13. This allows the measurement unit 15 to receive infrared radiation at a specific portion of the ear of the subject when in the wearing state of the measurement apparatus 10.

More particularly, for example, the measurement unit 15 can receive infrared radiation radiated from the subject's eardrum. The eardrum, by virtue of being located in an inner part of the ear, is not as affected by outside air. Thus, by receiving infrared radiation radiated from the eardrum, the measurement apparatus 10 can easily and accurately measure the body temperature of the subject.

Next, sound to be outputted from the measurement apparatus 10 will be described.

Sound outputted from the sound output unit 16 is configured to pass through the inside of the metal tube 13 and then be outputted to the outside of the measurement apparatus 10. Here, as described above, in the present embodiment, the length L of the metal tube 13 is longer than the diameter D thereof by a predetermined amount or more. The metal tube 13 has acoustic characteristics such that amplitudes at predetermined frequencies (resonance frequencies) would be amplified by resonance.

Figure 2:
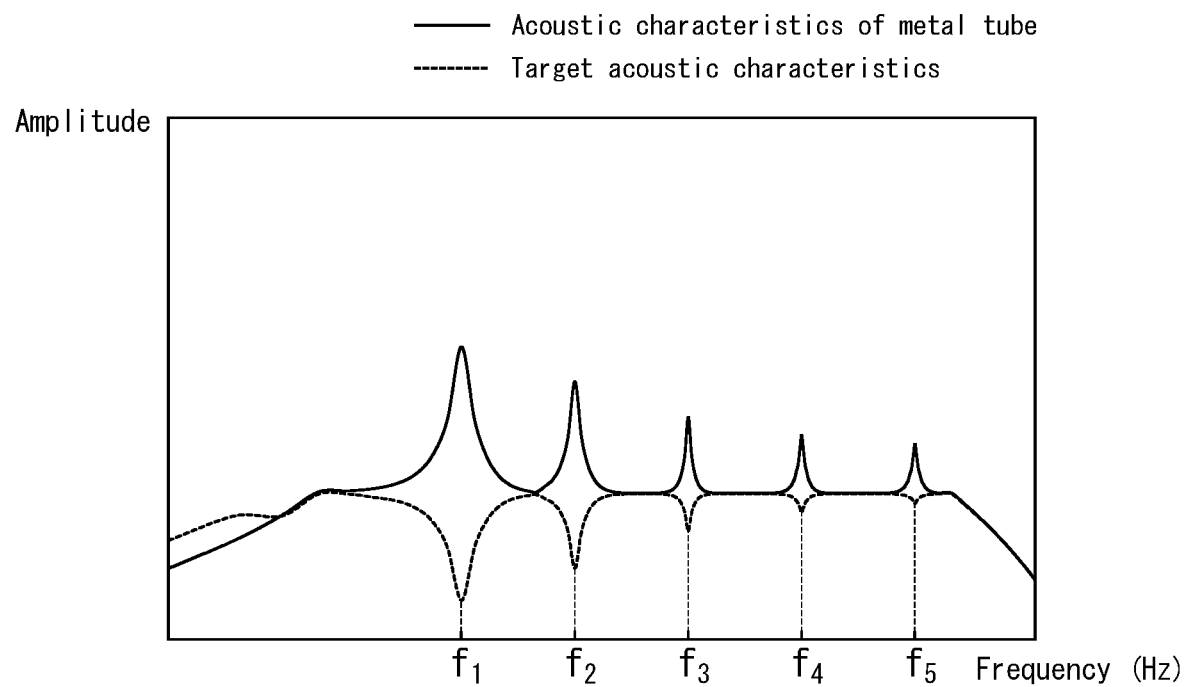
FIG. 2 illustrates an example of acoustic characteristics.

For example, as indicated by the solid line in FIG. 2, the metal tube 13 has acoustic characteristics such that amplitudes at the predetermined frequencies $f_1$, $f_2$, $f_3$, $f_4$ and $f_5$ are higher than those in other frequency ranges. Thus, when the characteristics of the sound inputted to the first end 13a of the metal tube 13 are uniform, sound at the predetermined frequencies $f_1$, $f_2$, $f_3$, $f_4$ and $f_5$ is amplified more than sound in other frequency ranges due to the acoustic characteristics of the metal tube 13, and is then outputted from the second end 13b. That is, in this case, sound outputted at the predetermined frequencies $f_1$, $f_2$, $f_3$, $f_4$ and $f_5$ is be stronger than that outputted in other frequency bands. From the perspective of the subject listening to the sound, it is undesirable for the sound pressure per frequency to differ greatly.

In the measurement apparatus 10 according to the present embodiment, by setting the acoustic characteristics of sound to be inputted to the first end 13a of the metal tube 13 to predetermined acoustic characteristics (hereinafter, also referred to as "target acoustic characteristics"), the acoustic characteristics of sound outputted from the second end 13b of the metal tube 13 can be improved. In the present description, as indicated by the broken line in FIG. 2, the target acoustic characteristics are such that amplitudes at the frequencies $f_1$, $f_2$, $f_3$, $f_4$ and $f_5$, at which sound would be amplified due to the acoustic characteristics of the metal tube 13, are smaller than those in other frequency bands. The target acoustic characteristics can be realized by the positional relationship between the metal tube 13, and the first opening 17a and the second opening 17b provided on the substrate 14. When sound having the acoustic characteristics with smaller amplitudes at the predetermined frequencies $f_1$, $f_2$, $f_3$, $f_4$ and $f_5$, as indicated by the broken line in FIG. 2, is inputted, sound of the predetermined frequency band would be amplified, as indicated by the solid line in FIG. 2 as the acoustic characteristics of the metal tube 13. As a result, sound having the characteristics of a smaller sound pressure difference for each frequency over the entire frequency band is outputted from the second end 13b of the metal tube 13.

Next, the target acoustic characteristics of sound to be inputted to the first end 13a of the metal tube 13 will be further described.

Figure 3:
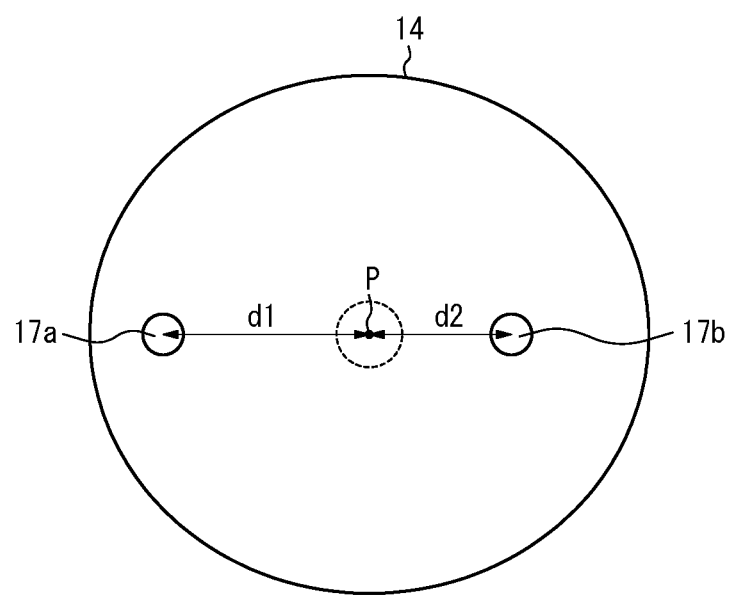
FIG. 3 is a top view of the substrate in FIG. 1.

FIG. 3 is a top view of the substrate 14 in FIG. 1, as viewed from the first surface 14a side. As illustrated in FIG. 3, the first opening 17a, the second opening 17b and the point P are provided on a straight line. The broken line in FIG. 3 indicates a line obtained by projecting the metal tube 13 onto the first surface 14a of the substrate 14. The first opening 17a and the second opening 17b are provided on the substrate 14 at positions with different distances from the point P. That is, when the distance between the center of the first opening 17a and the point P is d1, and the distance between the center of the second opening 17b and the point P is d2, the lengths of distance d1 and distance d2 are different. In the example illustrated in FIG. 3, d1>d2.

When the distance d1 and the distance d2 are different, the first path via the first opening 17a and the second path via the second opening 17b, through which sound outputted from the sound output unit 16 passes to reach the first end 13a of the metal tube 13, are different in distance. As illustrated in FIG. 1, the first path has a distance D1 from the sound output unit 16 to the first end 13a, and the second path has a distance D2 from the sound output unit 16 to the first end 13a. Since the distance d1 and the distance d2 are different as described with reference to FIG. 3, the distance D1 and the distance D2 are also different. When d1>d2 as illustrated in FIG. 3, D1>D2.

When the difference ΔD between the distance D1 and the distance D2 is (n+½) times the wavelength of sound, where n is an integer greater than or equal to 0, sound passing through the first opening 17a and sound passing through the second opening 17b weaken each other due to the interference of the sound. Here, of the frequencies at which sound would be amplified due to the acoustic characteristics of the metal tube 13, the fundamental frequency is f, and the wavelength of sound at the fundamental frequency f is fundamental wavelength λ. That is, the frequencies $f_1$, $f_2$, $f_3$, $f_4$ and $f_5$ in FIG. 2 are represented by mf, where m is an integer greater than or equal to 0. In this case, according to the interference of the sound described above, by providing the first opening 17a and the second opening 17b at positions satisfying ΔD=λ(n+½), the target acoustic characteristics indicated by the broken line in FIG. 2 according to which the amplitudes at the predetermined frequencies $f_1$, $f_2$, $f_3$, $f_4$ and $f_5$ are smaller can be realized.

The fundamental wavelength λ is determined by the length L of the metal tube 13. Thus, by providing the first opening 17a and the second opening 17b at positions satisfying ΔD(=|D1−D2|)=L(n+½) the target acoustic characteristics can be realized. In the present embodiment, the first opening 17a and the second opening 17b are provided on the substrate 14 so as to satisfy ΔD=L(n+½). Thereby, sound having the target acoustic characteristics indicated by the broken line in FIG. 2 is inputted to the first end 13a. As a result, sound having the characteristics with a smaller sound pressure difference for each frequency over the entire frequency band is outputted from the second end 13b. In this manner, the acoustic characteristics of the measurement apparatus 10 according to the present embodiment can be improved.

Figure 4:
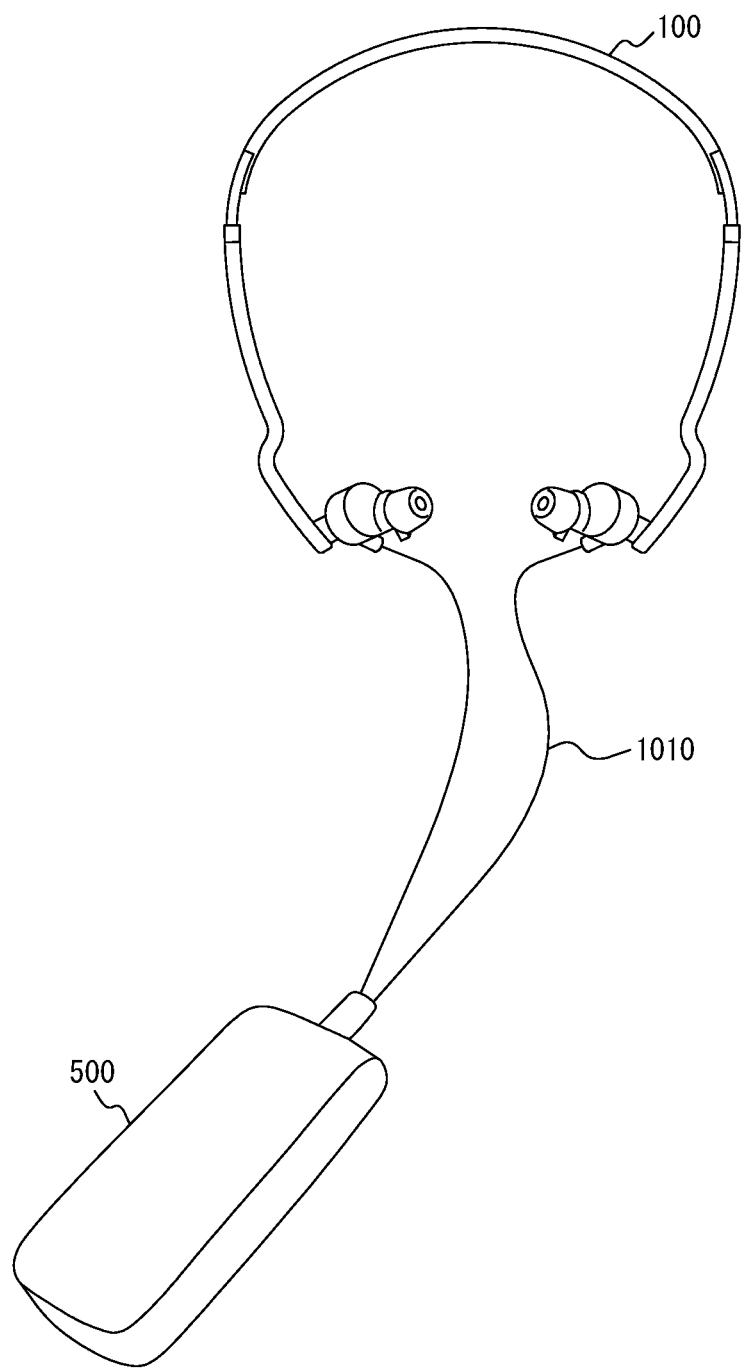
FIG. 4 is a schematic diagram illustrating a connection configuration of a measurement instrument and a control apparatus.

The measurement apparatus 10 can be mounted on a measurement instrument. FIG. 4 is a schematic diagram illustrating a connection configuration of a measurement instrument 100 and a control apparatus 500. As illustrated in FIG. 4, the control apparatus 500 is connected to the measurement instrument 100 by a cord 1010. The control apparatus 500 and the measurement instrument 100 transmit and receive information and power via the cord 1010. In addition to the wired cord 1010, the control apparatus 500 and the measurement instrument 100 may transmit and receive information and power in a wireless manner. This wireless manner can be anything such as Bluetooth® (Bluetooth is a registered trademark in Japan, other countries, or both), infrared radiation, NFC (Near Field Radio Communication), or the like. Further, the measurement instrument 100 may include a battery such as a cell or the like.

The measurement instrument 100 may be constituted, for example, by a headband type earphone. The measurement instrument 100 may, for example, be wearable on a subject's head. Further, the measurement instrument 100 may be configured to include the measurement apparatus 10 in a part to be inserted into an ear.

Figure 5:
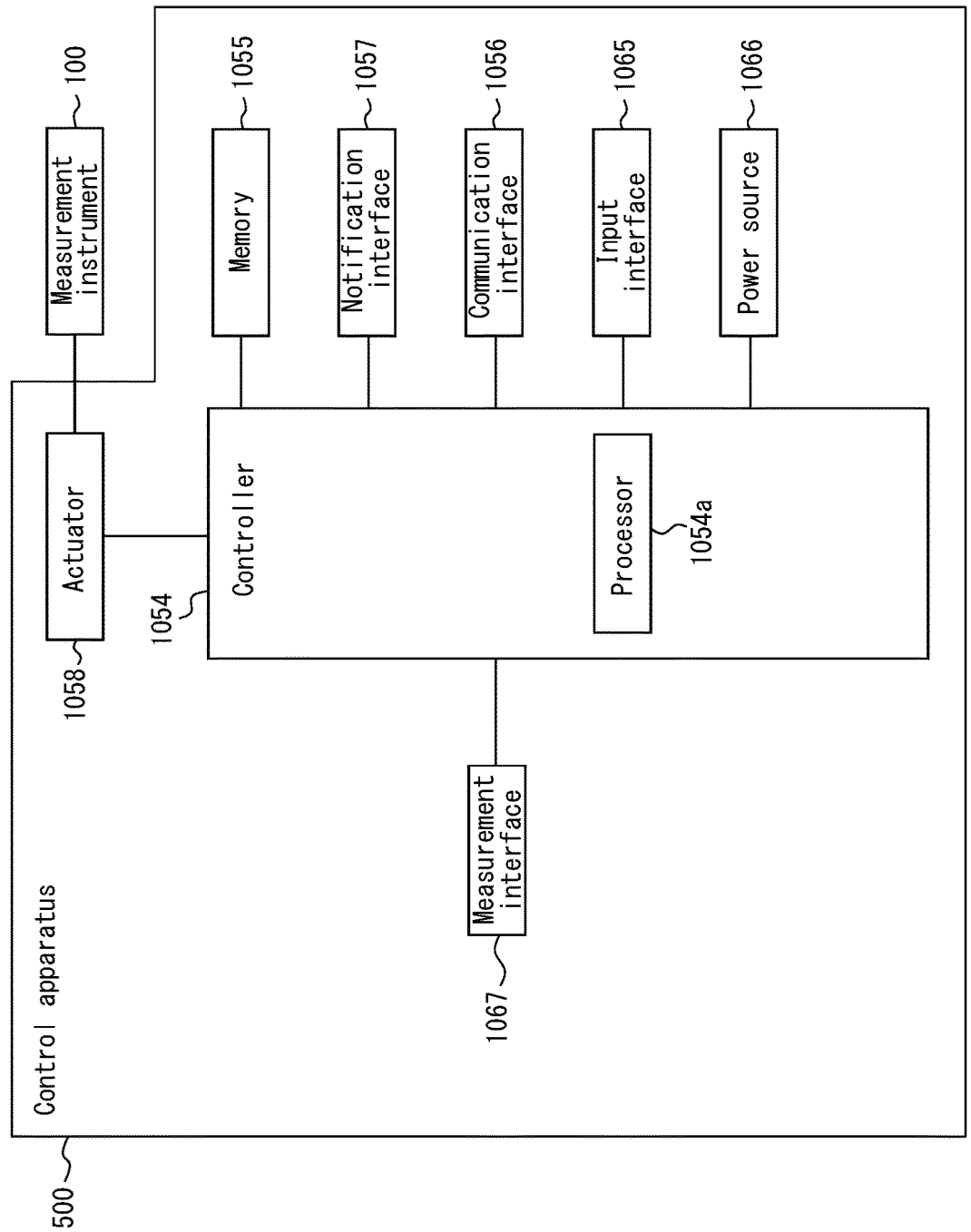
FIG. 5 illustrates an example of functional blocks provided with the control apparatus in FIG. 4.

Next, the internal structure of the control apparatus 500 illustrated in FIG. 4 will be described with reference to FIG. 5. FIG. 5 illustrates an example of functional blocks included in the control apparatus 500 illustrated in FIG. 4. The control apparatus 500 is configured to control the sound output of the measurement apparatus 10.

The control apparatus 500 includes a measurement interface 1067, a controller 1054, a memory 1055, a communication interface 1056, a notification interface 1057, an actuator 1058, an input interface 1065, and a power source 1066 as functional units.

The controller 1054 includes at least one processor 1054a for controlling and managing the whole control apparatus 500, including each functional block of the control apparatus 500. The controller 1054 includes at least one processor 1054a such as a CPU (Central Processing Unit) configured to execute a program prescribing a control procedure, and thus enables its function. Such a program is stored in, for example, the memory 1055 or an external storage medium connected to the control apparatus 500.

According to various embodiments of the present disclosure, the at least one processor 1054a may be realized as a single integrated circuit (IC), or a plurality of communicably connected integrated circuits and/or discrete circuits. Further, the at least one processor 1054a can be performed in accordance with various known techniques.

In one embodiment according to the present disclosure, the processor 1054a may include one or more circuits or units, configured to perform one or more data calculation procedures or processes by executing instructions stored in an associated memory. In another embodiment according to the present disclosure, the processor 1054a may be a firmware, for example, a discrete logic component, configured to perform one or more data calculation procedures or processes.

According to various embodiments of the present disclosure, the processor 1054a may include one or more processors, a controller, a microprocessor, a microcontroller, an application specific integrated circuit (ASIC), a digital signal processor, a programmable logic device, a field programmable gate array, any combination of these devices or configurations, or any combination of other known devices or configurations; and thus perform the functions as the controller 1054 described later.

The controller 1054 controls the output of sound from the sound output unit 16 of the measurement apparatus 10. Further, the controller 1054 measures or calculates the subject's body temperature based on biological information measured by the measurement unit 15 of the measurement apparatus 10.

The memory 1055 can be constituted by a semiconductor memory, a magnetic memory, or the like. The memory 1055 stores various kinds of information and/or a program for operating the control apparatus 500, and the like. The memory 1055 may also function as a working memory. The memory 1055 may, for example, store a body temperature calculated by the controller 1054.

In the memory 1055, music information and other sound information to be outputted from the sound output unit 16 of the measurement instrument 100 is stored. The controller 1054 is configured to extract predetermined sound information from the memory 1055 based on an input operation or the like by the user, and output the extracted information to the sound output unit 16 of the measurement instrument 100 via the actuator 1058. Based on the received sound information, the sound output unit 16 outputs sound.

Here, sound data to be stored in the memory 1055 will be described with reference to FIG. 6. FIG. 6 is a conceptual diagram of sound data to be stored in the memory 1055.

As illustrated in FIG. 6, sound data of health information 600, music information 630 and environment information 650 are stored in the memory 1055. The health information 600 includes, for example, information 601 for notification of "the body temperature is higher than average", and information 603 for notification of "the body temperature is lower than average". The average here may, for example, be an average of a typical adult or an average of a subject. In the present disclosure, the health information 600 is not limited to those illustrated in FIG. 6, and may be any other sound information.

The music information 630 includes, for example, pieces of music information 631, 633, 635, 637, 639 and 641. In the present disclosure, the music information is not limited to six pieces, and may be any number.

The environment information 650 includes, for example, sound information related to the surrounding environment of the measurement instrument 100, such as information 651 for notification of a temperature rise after a predetermined time, information 653 for notification of a temperature fall after a predetermined time, information 655 for notification of a rainfall after a predetermined time, and the like. In the present disclosure, the environment information 650 is not limited to those illustrated in FIG. 6, and may be any other environment information, such as information for notification of a snowfall or a fog, information related to road conditions such as a traffic jam or a traffic accident, and information related to operation status of a train, a bus, an airplane, and the like.

The communication interface 1056 transmits and receives various kinds of information by communicating with an external device via a network. The external device that the communication interface 1056 communicates with may, for example, be server, a PC (Personal Computer), a mobile phone, a smartphone, a tablet, a wristwatch, a massage machine, any other devices, or any combinations of these. The communication interface 1056 transmits and receives information to and from the external device using a network configured in a wireless manner, a wired manner, or a combination of these. For example, the communication interface 1056 can use, for example, Bluetooth, infrared radiation, NFC, wireless LAN (Local Area Network), wired LAN, any other communication mediums, or any combinations of these. The communication interface 1056 acquires biological information related to body temperature measured by the measurement unit 15 by communicating with the measurement instrument 100.

The notification interface 1057 notifies information by sound, light, image, vibration, or other appropriate methods. The notification interface 1057 may be constituted, for example, by a liquid crystal display, a speaker, a LED (Light Emitting Diode), a vibrator, any other notification members, or any combination of these. The notification interface 1057 may notify, for example, information related to a measured body temperature.

The actuator 1058 outputs a signal for actuating the sound output unit 16 based on a control signal from the controller 1054.

The input interface 1065 is configured to receive input operations made by the subject using the control apparatus, and is constituted, for example, by operation buttons (operation keys). The input interface 1065 may also be constituted by a touch panel, and on a part of the display device, operation keys may be displayed to receive touch operation input by a subject.

The power source 1066 is a battery for supplying power for the control apparatus 500 to perform various operations.

The measurement interface 1067 is configured to measure the surrounding environment and the like. In the present disclosure, the measurement interface 1067 is a thermometer for measuring the temperature at a predetermined portion. In the present disclosure, the predetermined portion is a part of human body, thus, the temperature is body temperature, and the thermometer is a clinical thermometer. The measurement interface 1067 may, for example, be a clinical thermometer, a thermometer, a hygrometer, an altimeter, any other measurement instruments, or any combinations of these. The measurement interface 1067 is capable of measuring body temperature, temperature, humidity, altitude and other data in an environment in which the control apparatus 500 is arranged.

The controller 1054 may be configured to acquire weather information for a date and time when a body temperature is measured, from a weather information server connected to the control apparatus 500 via a network, and then transmit the acquired information to a server 1000.

Figure 7:
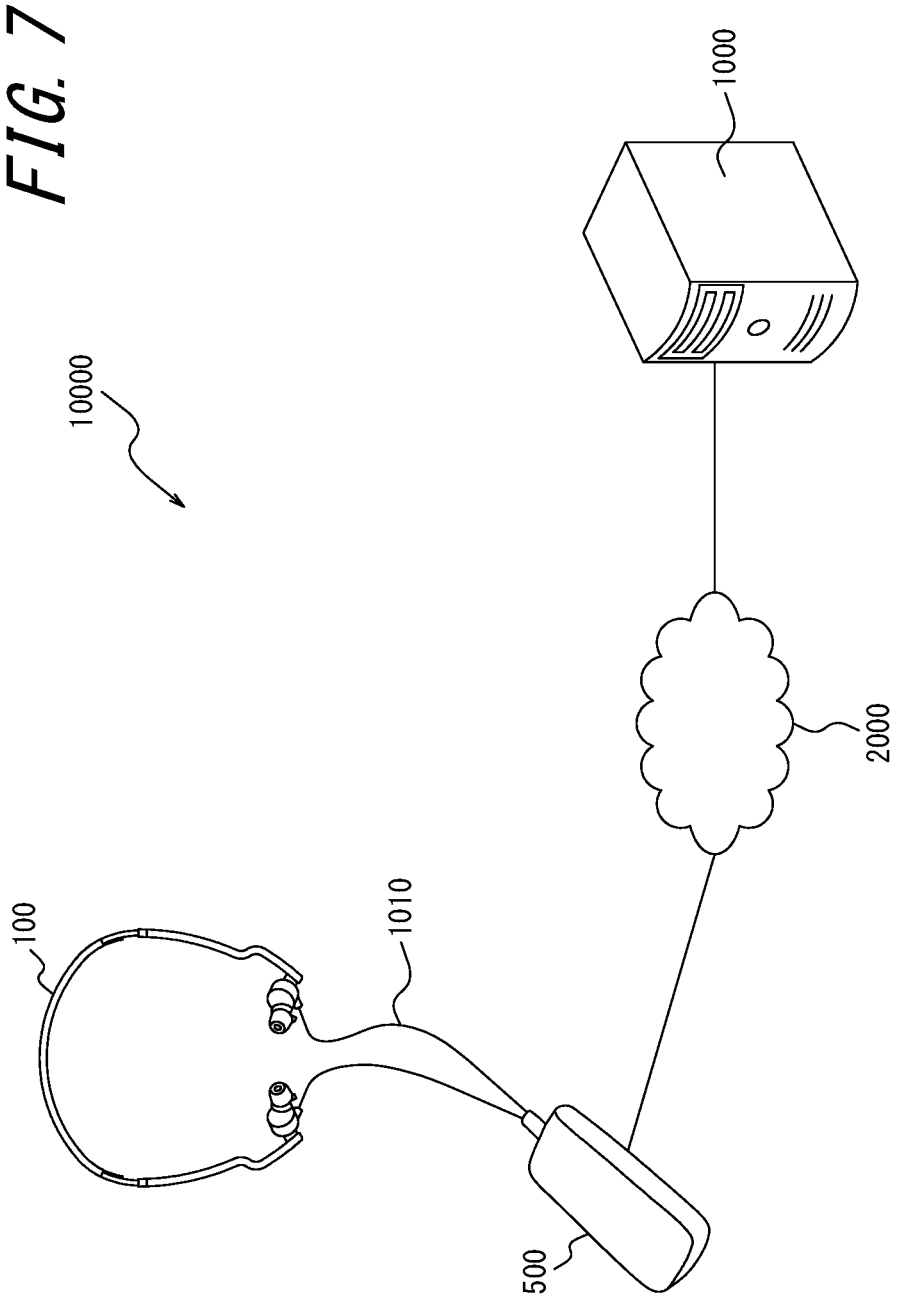
FIG. 7 is a schematic diagram illustrating a configuration example of a measurement system in which the measurement instrument in FIG. 4 is used.

Next, a measurement system 10000 in which the measurement instrument 100 illustrated in FIG. 4 is used will be described with reference to FIG. 7. As illustrated in FIG. 7, the control apparatus 500 connected to the measurement instrument 100 is also connected to the server 1000 via a network 2000. In the measurement system 10000, the server 1000 may be a PC, a mobile phone, a smartphone, a tablet, a wristwatch, a massage machine, any other devices, or any combination of these.

In the present disclosure, the measurement instrument 100 transmits and receives information to and from the server 1000 connected to the network 2000 via the control apparatus 500. However, the measurement instrument 100 may be directly connected to the network 2000 to transmit and receive information to and from the server 1000.

The network 2000 in the present disclosure may be the Internet. However, the network 2000 is not limited to this, and may be any appropriate network. Further, the network 2000 may be configured in a wireless manner, a wired manner, or a combination of these. That is, the control apparatus 500 and the server 1000 may be connected by the network 2000 configured in a wired manner, a wireless manner, or a combination of these, to transmit and receive information to and from each other. In addition, in the present disclosure, the server 1000 and the network 2000 are not limited to one, and each may be at least one or more.

Figure 8:
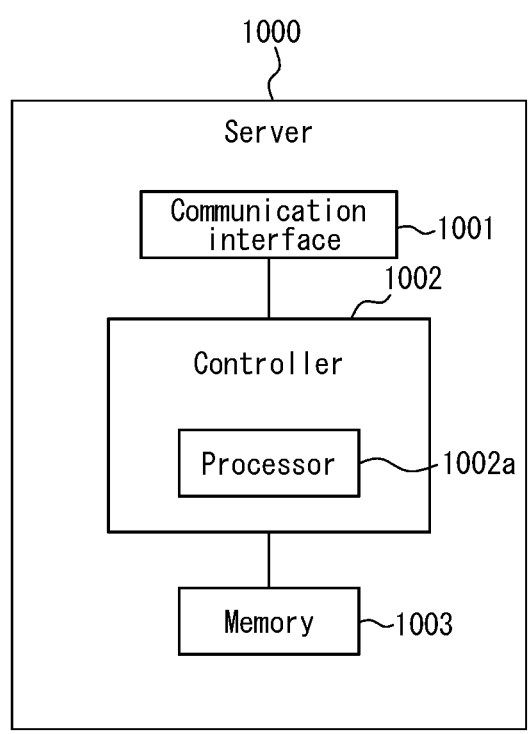
FIG. 8 is a functional block diagram illustrating a schematic configuration of the server in FIG. 7.

Next, the internal structure of the server 1000 illustrated in FIG. 7 will be described with reference to FIG. 8. FIG. 8 is a functional block diagram illustrating the schematic configuration of the server 1000 in FIG. 7. The server 1000 includes a communication interface 1001, a controller 1002, and a memory 1003.

The communication interface 1001 transmits and receives various kinds of information by communicating with the control apparatus 500 via the network 2000. This network 2000 may be configured in a wireless manner, a wired manner, or a combination of these. For example, the communication interface 1001 can use Bluetooth, infrared radiation, NFC, wireless LAN, wired LAN, WAN (Wide Area Network), the Internet, any other communication mediums, or any combination of these to perform communication. In the present embodiment, the communication interface 1001 uses the Internet to communicate with the control apparatus 500.

The controller 1002 includes at least one processor 1002a for controlling and managing the whole server 1000, including each functional block of the server 1000. The controller 1002 includes at least one processor 1002a such as a CPU configured to execute a program prescribing a control procedure, and thus enables its function. Such a program is stored in, for example, the memory 1003 or an external storage medium connected to the server 1000.

According to various embodiments of the present disclosure, the at least one processor 1002a may be performed as a single integrated circuit (IC), or as a plurality of communicably connected integrated circuits and/or discrete circuits. Further, the at least one processor 1002a can be implemented in accordance with various known techniques.

In one embodiment according to the present disclosure, the processor 1002a may include one or more circuits or units, configured to perform one or more data calculation procedures or processes by executing instructions stored in an associated memory. In another embodiment according to the present disclosure, the processor 1002a may be firmware, for example, a discrete logic component, configured to perform one or more data calculation procedures or processes.

According to various embodiments of the present disclosure, the processor 1002a may include one or more processors, a controller, a microprocessor, a microcontroller, an application specific integrated circuit (ASIC), a digital signal processor, a programmable logic device, a field programmable gate array, any combination of these devices or configurations, or any combination of other known devices or configurations; and thus perform the functions as the controller 1002.

The memory 1003 can be constituted by a semiconductor memory, a magnetic memory, or the like. The memory 1003 stores various kinds of information and/or a program for operating the server 1000, and the like. The memory 1003 may also function as a working memory. The memory 1003 may, for example, store various kinds of information acquired by the server 1000 from the communication interface 1001.

The server 1000 is configured to receive information related to body temperature from the control apparatus 500. Then, the server 1000 analyzes the received information, and transmits a result indicating the analysis to the control apparatus 500. Further, the server 1000 is capable of receiving other information such as air temperature, weather, disaster information and the like via the network 2000.

The server 1000 may store information received from the control apparatus 500 in the memory 1003, as standalone information or in association with user's personal information. The server 1000 may be managed by a company to which the user belongs, a government, a public organization, a medical institution, a health management organization, an insurance company, or the like.

In the example illustrated in FIG. 7, there is one server 1000. However, the present disclosure in not limited to this, and the server 1000 may be any number greater than or equal to one. In this case, a plurality of servers 1000 may be configured to perform the same processing, or perform the processing illustrated in FIG. 9 described later in a distributed manner, or perform a combination of these.

Figure 9:
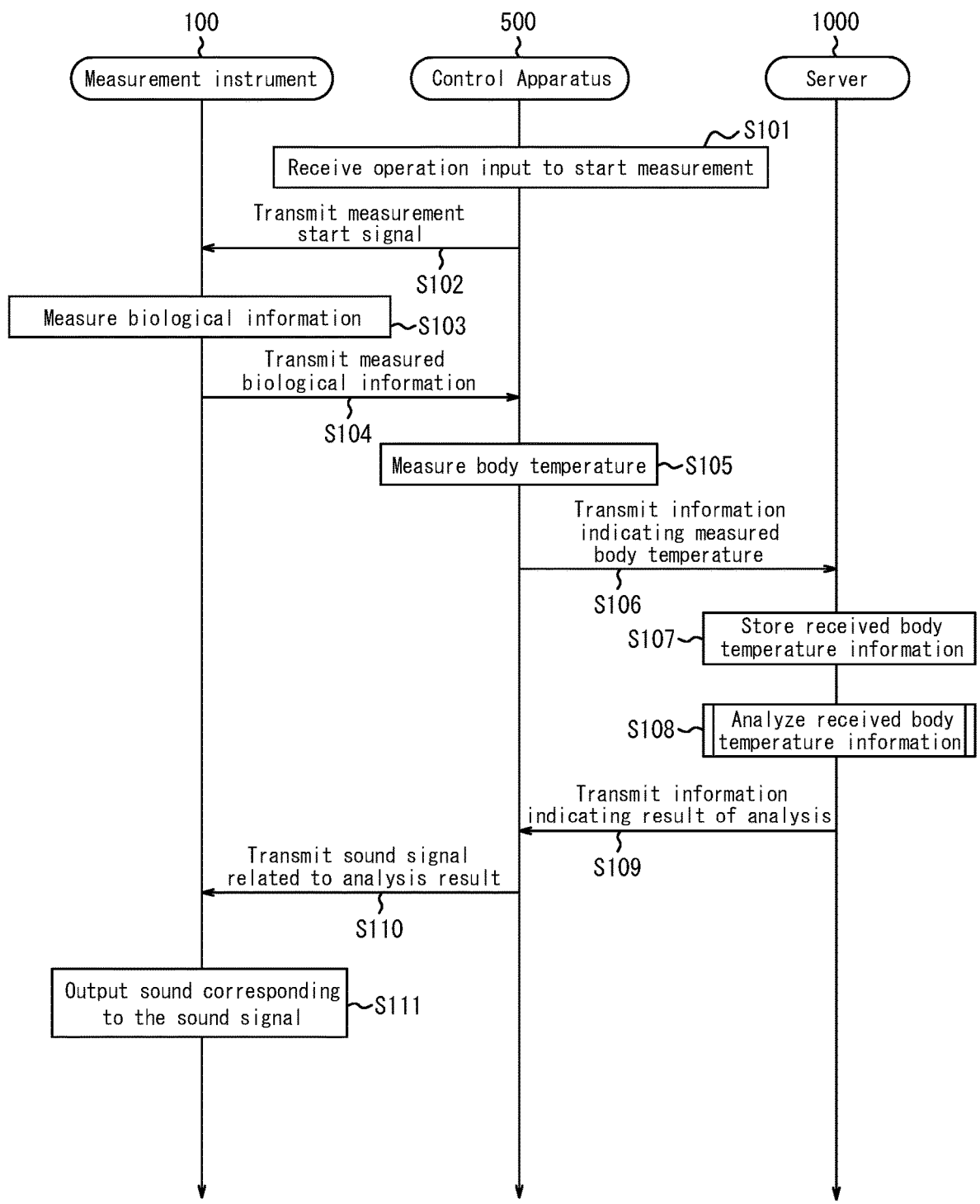
FIG. 9 is a sequence chart illustrating an example of processing performed by the measurement system in FIG. 7.

Next, an example of processing by the measurement system 10000 will be described. FIG. 9 is a sequence chart illustrating an example of processing by the measurement system 10000. The sequence illustrated in FIG. 9 may be started, for example, according to a state in which a user is wearing the measurement instrument 100.

Initially, the control apparatus 500 receives an operation input to start measurement from a subject (Step S101).

Upon receiving the operation input, the control apparatus 500 transmits a measurement start signal to the measurement instrument 100 (Step S102).

Based on the measurement start signal, the measurement instrument 100 measures biological information using the measurement unit 15 of the measurement apparatus 10 (Step S103).

Then, the measurement instrument 100 transmits the biological information measured by the measurement unit 15 to the control apparatus 500 (Step S104).

Based on the biological information acquired from the measurement instrument 100, the control apparatus 500 measures the body temperature of the subject (Step S105).

Then, the control apparatus 500 transmits information related to the measured body temperature (hereinafter, also referred to as "body temperature information") to the server 1000 (Step S106).

Upon receiving the body temperature information from the control apparatus 500, the server 1000 stores the received body temperature information in the memory 1003 (Step S107).

Further, the server 1000 analyzes the body temperature information received from the control apparatus 500 (Step S108). Details of the analysis of the body temperature information will be described later.

Then, the server 1000 transmits information indicating a result of the analysis to the control apparatus 500 (Step S109).

Based on the received analysis result, the control apparatus 500 transmits a sound signal related to the analysis result to the measurement instrument 100 (Step S110).

Then, the measurement instrument 100 outputs a sound corresponding to the sound signal from the sound output unit 16 (Step S111). Through the output of the sound, the subject can be notified of the analysis result.

In Step S110, the control apparatus 500 may output a notification corresponding to the analysis result from the notification interface 1057 without transmitting the sound signal.

Next, the data to be stored in the server 1000 illustrated in FIG. 7 will be described with reference to FIGS. 10A, 10B, 10C, and 10D. FIGS. 10A, 10B, 10C, and 10D are configuration diagrams illustrating examples of data to be stored in the server 1000 illustrated in FIG. 7. The information illustrated in FIGS. 10A, 10B, 10C, and 10D may be acquired by measurement, by the server 1000 via the network 2000, or by user's input.

FIG. 10A illustrates a data structure D10 with user ID 3001 and measurement date and time 3003 as primary keys. Here, in FIGS. 10A, 10B, 10C, and 10D, a black dot is attached to each primary key. At least one or more data of values corresponding to attributes of each column are stored in each column.

User ID 3001 is a value that uniquely corresponds to a user. Measurement date and time 3003 is a value of the date and time when the biological information was measured. The measurement date and time may have a certain range, such as an hour (for example, from 0:00 to 1:00), a time period (for example, in the morning), a date (for example, January 1), a month (for example, January), a plurality of months (for example, from January to March), a year (for example, 2100), or the like.

Body temperature 3005 is information related to a body temperature measured at the measurement date and time 3003 by a user identified by the user ID 3001. Weather 3007 is a value of the weather at the measurement date and time 3003. The temperature 3009 is information indicating the atmospheric temperature at measurement date and time 3003.

FIG. 10B illustrates a data structure D20 with the user ID 3001 as a primary key. Age 3011 is the age of the user identified by user ID 3001. Gender 3013 is the gender of the user identified by user ID 3001.

FIG. 10C illustrates a data structure D30 with measurement date and time 3003, weather 3007, temperature 3009, age 3011, and gender 3013 as primary keys. Average body temperature 3015 is an average value of body temperatures measured in a user group identified by measurement date and time 3003, weather 3007, temperature 3009, age 3011, and gender 3013. That is, average body temperature 3015 is an average body temperature of a group to which the user belongs.

FIG. 10D illustrates a data structure D40 with user ID 3001, measurement date and time 3003, weather 3007, and temperature 3009 as primary keys. Individual average body temperature 3017 is an average value of body temperatures of a specific user measured in a predetermined situation, and is identified by user ID 3001, measurement date and time 3003, weather 3007, and temperature 3009.

Figure 11:
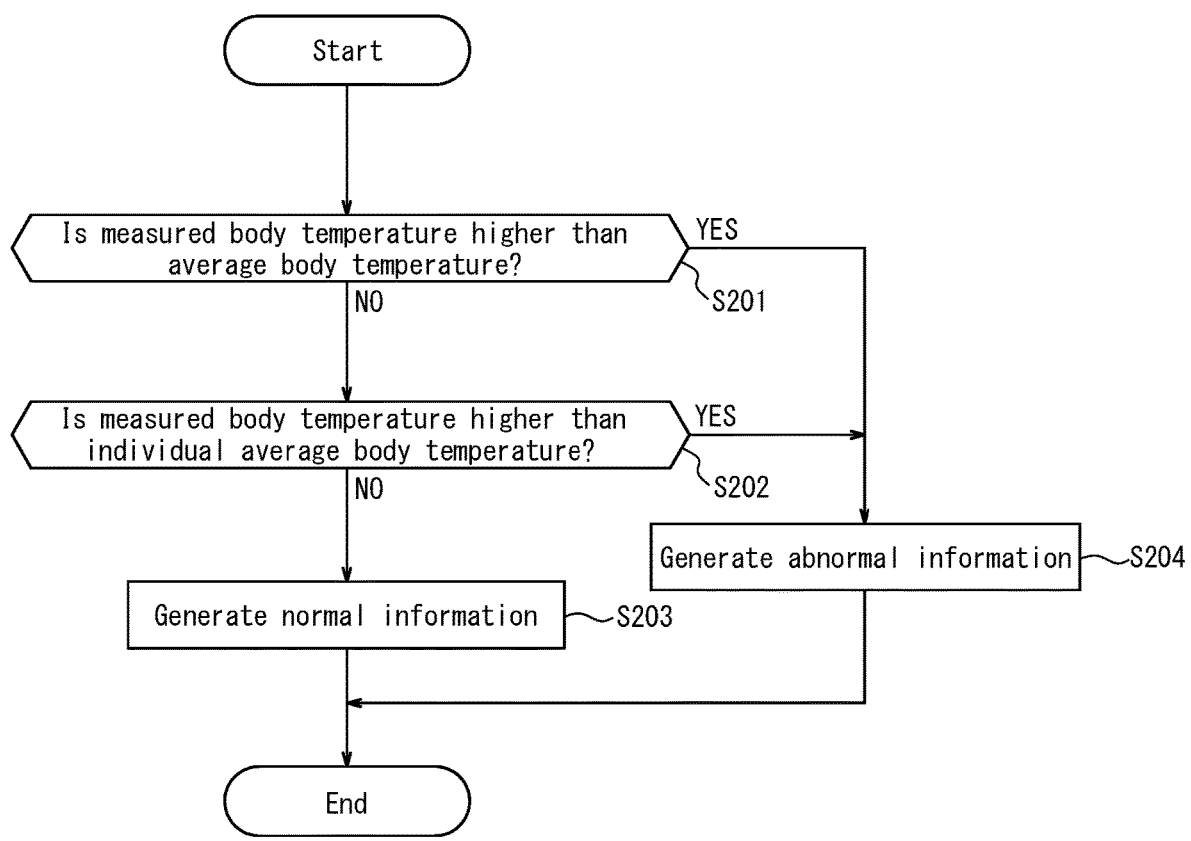
FIG. 11 is a flowchart illustrating an example of body temperature information analysis processing performed by the server in FIG. 7.

Next, analysis processing of body temperature information by the server 1000 illustrated in FIG. 7 will be described in detail with reference to FIG. 11. FIG. 11 is a flowchart illustrating an example of analysis processing of biological information by the server 1000 illustrated in FIG. 7. That is, FIG. 11 is a flowchart illustrating an example of the detailed processing of Step S108 illustrated in FIG. 9. The processing illustrated in FIG. 11 can be realized, for example, by the processor 1002a illustrated in FIG. 8 cooperating with the program stored in the memory 1003.

As described above, the server 1000 receives the body temperature information transmitted from the control apparatus 500 via the network 2000 in Step S106 illustrated in FIG. 9. At this time, the server 1000 may further acquire information regarding user ID, measurement date and time, weather, and temperature from the control apparatus 500.

Based on the acquired information, in Step S107, the server 1000 generates the data structure D10 illustrated in FIG. 10A and stores the same in the memory.

Then, the server 1000 determines whether the subject's body temperature indicated by the received body temperature information (hereinafter, also referred to as "measured body temperature") is higher than the average body temperature in the data structure D30 illustrated in FIG. 10C with reference to the data structure D10, the data structure D20, and the data structure D30 (Step S201).

When the measured body temperature is lower than the average body temperature in the data structure D30 illustrated in FIG. 10C (Step S201: No), the server 1000 then determines whether the measured body temperature is higher than the individual average body temperature in the data structure D40 illustrated in FIG. 10D with reference to the data structure D10 and the data structure D40 (Step S202).

When the measurement body temperature is lower than the individual average body temperature in the data structure D40 illustrated in FIG. 10D (Step S202: No), the server 1000 then generates normal information indicating that the measured result is normal (Step S203). This is because when the measured body temperature is lower than the individual average body temperature, it can be determined to be normal. The generated normal information is then transmitted to the control apparatus 500 as a result of the analysis in Step S109 illustrated in FIG. 9.

On the other hand, when the measured temperature is higher than the individual average body temperature in the data structure D40 illustrated in FIG. 10D (Step S202: Yes), the server 1000 generates abnormal information indicating that the measured result is abnormal (Step S204). This is because when the measured temperature is higher than the individual average body temperature, it can be determined to be abnormal. The generated abnormal information is then transmitted to the control apparatus 500 a result of the analysis in Step S109 illustrated in FIG. 9.

Further, when the measured body temperature is higher than the average body temperature in the data structure D30 illustrated in FIG. 10C (Step S201: Yes), the server 1000 generates abnormal information indicating that the measured result is abnormal (Step S204). This is because when the measured body temperature is higher than the average body temperature, it can be determined to be abnormal. The generated abnormal information is then transmitted to the control apparatus 500 as a result of the analysis in Step S109 illustrated in FIG. 9.

Upon receiving the analysis information from the server 1000, the control apparatus 500 transmits a sound signal related to the analysis result, based on the normal information or the abnormal information included in the analysis information, to the measurement instrument 100 (Step S110). Then, the measurement instrument 100 outputs a sound corresponding to the sound signal (Step S111). In addition to sound, the measurement instrument 100 may notify the analysis result by light, image, vibration, other notification means, or any combination of these.

It has been described that the first opening 17a, the second opening 17b, and the point P are arranged on a straight line in the present embodiment, however, the first opening 17a, the second opening 17b, and the point P are not necessarily to be arranged on a straight line. The first opening 17a and the second opening 17b may be arranged at any positions on the substrate 14 that satisfy $\Delta D = L(n+\frac{1}{2})$.

Embodiment 2

Figure 12:
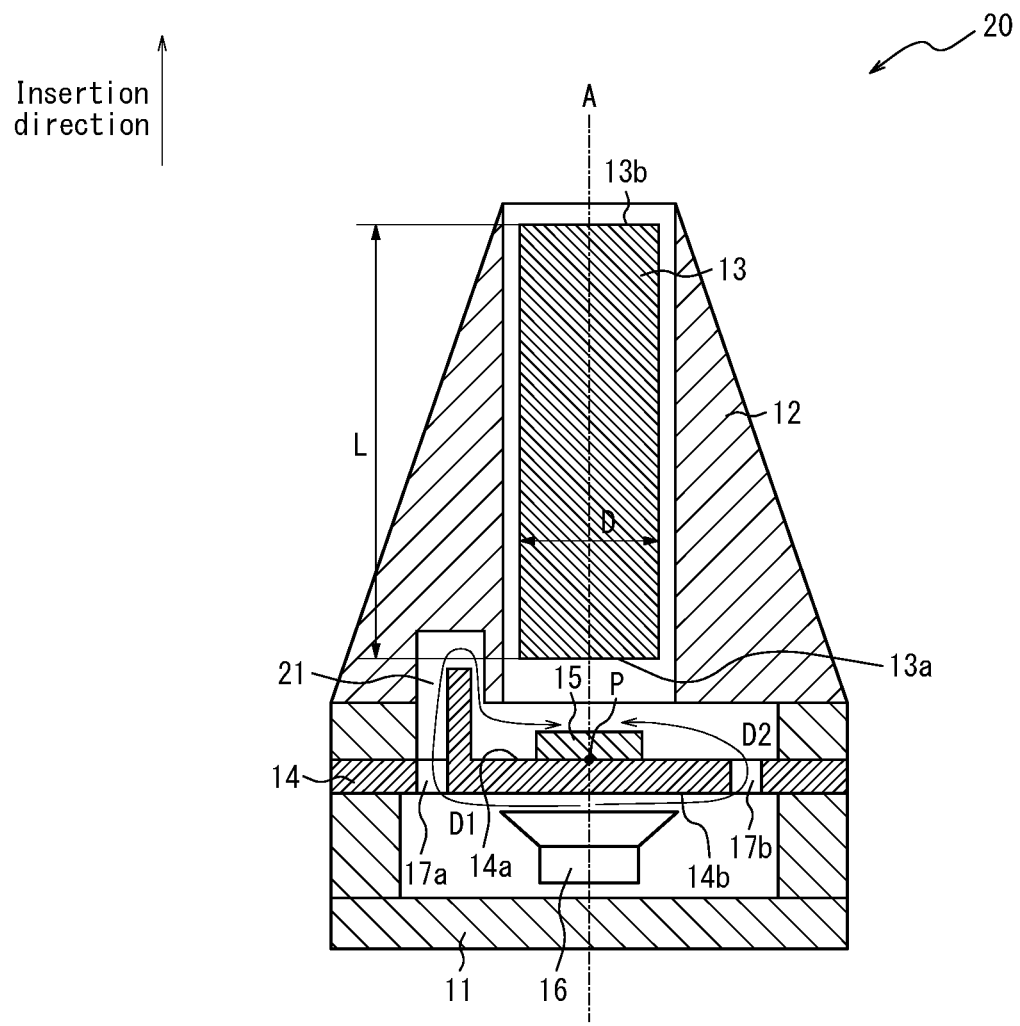
FIG. 12 is a schematic diagram illustrating the internal structure of a measurement apparatus according to Embodiment 2.

FIG. 12 is a schematic diagram illustrating the internal structure of a measurement apparatus 20 according to Embodiment 2. With respect to the measurement apparatus 20 according to Embodiment 2, description of points similar to those of Embodiment 1 will be omitted, and different points will be described. In Embodiment 2, the same reference numbers are assigned to functional units similar to those of Embodiment 1.

In the measurement apparatus 20 according to the present embodiment, a duct 21 with a pipe-like shape is provided in the holder 11 and/or the earpiece 12. The duct 21 functions as a path, extending from an opening provided on the substrate 14 to the first end 13a of the metal tube 13, for sound outputted from the sound output unit 16. As illustrated in FIG. 12, the duct 21 is only connected to the first opening 17a, and is not connected to the second opening 17b.

In the present embodiment, the first path is a path from the sound output unit 16 to the first end 13a via the first opening 17a and through the duct 21; and similar to Embodiment 1, the second path is a path from the sound output unit 16 to the first end 13a via the second opening 17b. Further, in the present embodiment, the first opening 17a and the second opening 17b may be provided on the substrate 14 with equal distances or different distances from the point P.

In the present embodiment, the length of the duct 21 is determined so as to satisfy $\Delta D=|D1-D2|=L(n+\frac{1}{2})$. The difference $\Delta D$ between the distance D1 of the first path and the distance D2 of the second path occurs by virtue of the duct 21, and thus sound having the target acoustic characteristics indicated by the broken line in FIG. 2 is inputted to the first end 13a. As a result, sound having the characteristics of a smaller sound pressure difference for each frequency over the entire frequency band is outputted from the second end 13b. In this manner, the acoustic characteristics of the measurement apparatus 20 according to the present embodiment can also be improved. Further, it is to be noted that, in the present embodiment, when the first opening 17a and the second opening 17b are provided at different distances from the point P, the difference between the distance from the point P to the first opening 17a and the distance from the point P to the second opening 17b is also reflected in $\Delta D$.

In the example illustrated in FIG. 12, the duct 21 is only connected to the first opening 17a, and is not connected to the second opening 17b. However, the present embodiment in not limited to this. For example, the duct 21 may be connected to the second opening 17b instead of the first opening 17a. In addition, two ducts 21 with different lengths may be respectively connected to the first opening 17a and the second opening 17b. Also in these examples, the ducts 21 are provided such that the difference $\Delta D$ between the distance D1 of the first path and the distance D2 of the second path satisfies $\Delta D=L(n+\frac{1}{2})$. Thereby, the acoustic characteristics of the measurement apparatus 20 can be improved.

Embodiment 3

Figure 13:
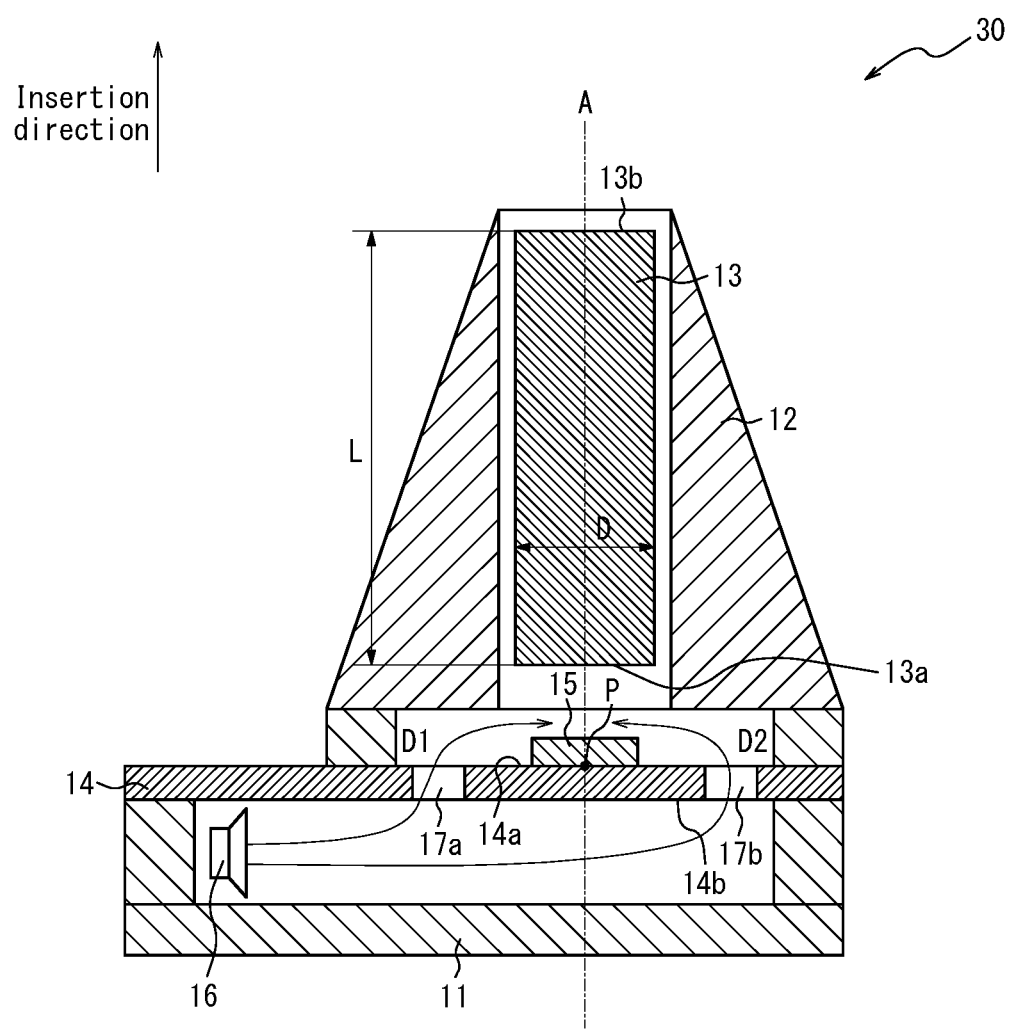
FIG. 13 is a schematic diagram illustrating the internal structure of a measurement apparatus according to Embodiment 3.

FIG. 13 is a schematic diagram illustrating the internal structure of a measurement apparatus 30 according to Embodiment 3. With respect to the measurement apparatus 30 according to Embodiment 3, description of points similar to those of Embodiment 1 will be omitted, and different points will be described. In Embodiment 3, the same reference numbers are assigned to functional units similar to those of Embodiment 1.

In the measurement apparatus 30 according to the present embodiment, the sound output unit 16 is provided at a position which does not intersect the axis A. The sound output unit 16, for example, in a top view, may be provided at a position separated from the point P by a distance larger than the distance d1 from the point P to the first opening 17a and the distance d2 from the point P to the second opening 17b. In the example illustrated in FIG. 13, the first opening 17a, the second opening 17b, the point P, and the sound output unit 16 are not provided on a straight line in the top view of the measurement apparatus 30. Further, the sound output unit 16 is provided on the opposite side of the second opening 17b with respect to the first opening 17a.

In this case, as illustrated in FIG. 13, the first path is a path from the sound output unit 16 to the first end 13a via the first opening 17a; and the second path is a path from the sound output unit 16 to the first end 13a through the second surface 14b of the substrate 14 and via the second opening 17b. The positions of the first opening 17a and the second opening 17b on the substrate 14, and the position of the sound output unit 16 in the measurement apparatus 30 are determined appropriately so as to satisfy $\Delta D=|D1-D2|=L(n+\frac{1}{2})$. Thereby, sound having the target acoustic characteristics indicated by the broken line in FIG. 2 is inputted to the first end 13a. As a result, sound having the characteristics of a smaller sound pressure difference for each frequency over the entire frequency band is outputted from the second end 13b. In this manner, the acoustic characteristics of the measurement apparatus 30 according to the present embodiment can also be improved.

Figure 14:
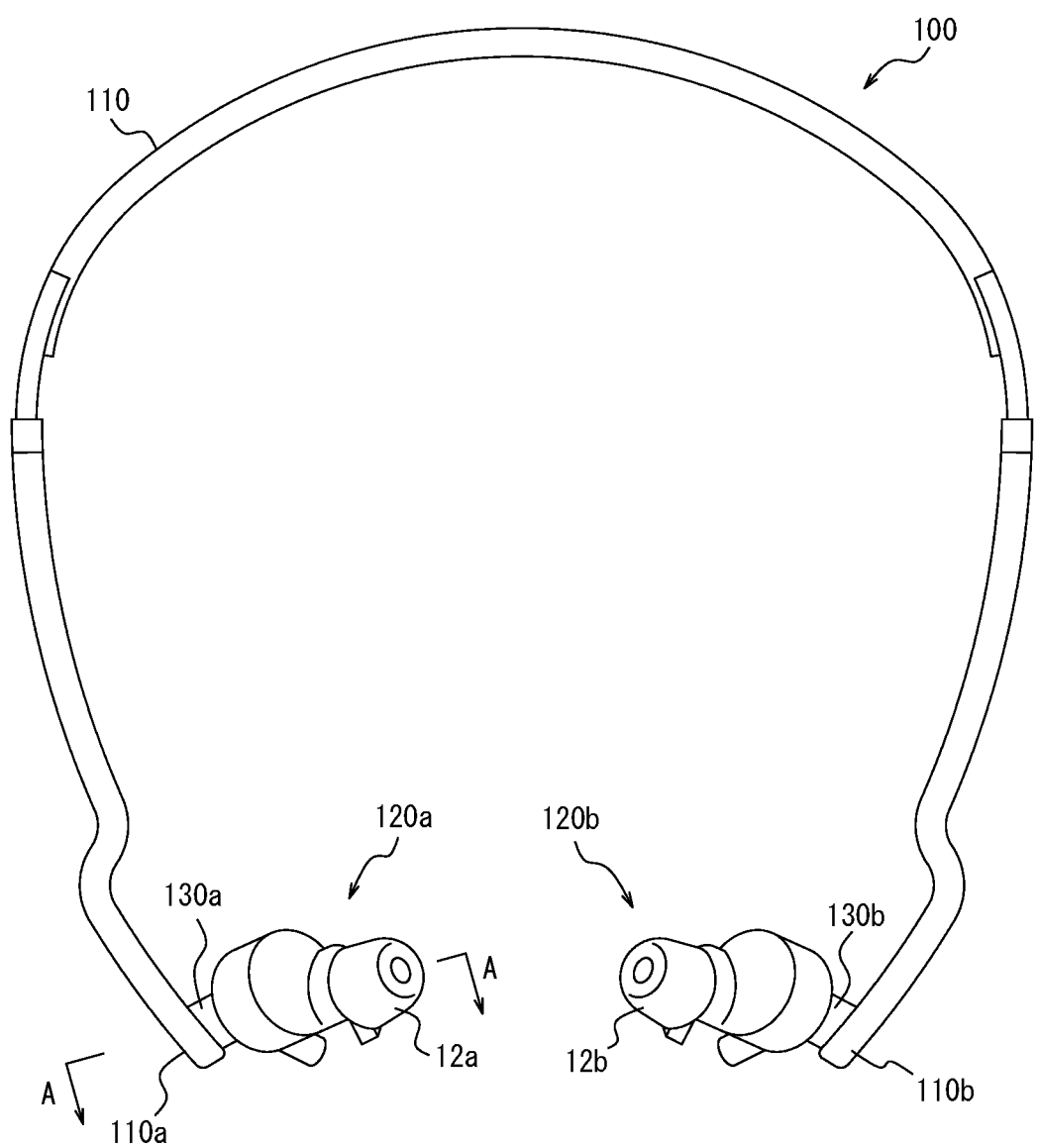
FIG. 14 is a schematic diagram illustrating the appearance of a measurement instrument provided with the measurement apparatus in FIG. 13.

FIG. 14 is a schematic diagram illustrating the appearance of the measurement instrument 100 provided with the measurement apparatus 30. The measurement instrument 100, as an example illustrated in FIG. 14, can be configured as a headband type earphone. The measurement instrument 100 includes a wearing portion 110, a first measurement portion 120a and a second measurement portion 120b, and a first connector 130a and a second connector 130b. The measurement instrument 100 may, for example, be wearable on a subject's head.

The wearing portion 110 is a mechanism for keeping the wearing state of the measurement instrument 100 to a subject. In the present embodiment, the wearing portion 110, for example, has an arch shape as illustrated in FIG. 14. A subject can wear the measurement instrument 100 by sandwiching the head with the wearing portion 110. The wearing portion 110 may, for example, have a mechanism such that the length of the wearing portion 110 can be adjusted according to the size of the subject's head. The wearing portion 110 may be formed from plastic or the like.

The first measurement portion 120a is provided at the first end 110a of the wearing portion 110, and is connected to the wearing portion 110 via the first connector 130a; and the second measurement portion 120b is provided at the second end 110b of the wearing portion 110, and is connected to the wearing portion 110 via the second connector 130b. That is, the wearing portion 110, the first measurement portion 120a and the second measurement portion 120b, and the first connector 130a and the second connector 130b, are configured as one measurement instrument 100 which is connected as a whole. The first connector 130a is formed at a portion connecting the first measurement portion 120a and the first end 110a of the wearing portion 110, and the second connector 130b is formed at a portion connecting the second measurement unit 120b and the second end 110b of the wearing portion 110.

The first measurement portion 120a and the second measurement portion 120b are the measurement apparatus 30 illustrated in FIG. 13 realized in the measurement instrument 100. That is, the first measurement portion 120a and the second measurement portion 120b have a configuration similar to that of the measurement apparatus 30. The first measurement portion 120a and the second measurement portion 120b may, for example, be configured symmetrically and have similar functions. In the present description, when there is no need to distinguish the first measurement portion 120a and the second measurement portion 120b, these are collectively referred to as measurement portion 120.

The first measurement portion 120a is configured to measure body temperature in the right ear when the earpiece 12a is inserted in the concha of the right ear; and the second measurement 120b is configured to measure body temperature in the left ear when the earpiece 12b is inserted in the left ear.

Figure 15:
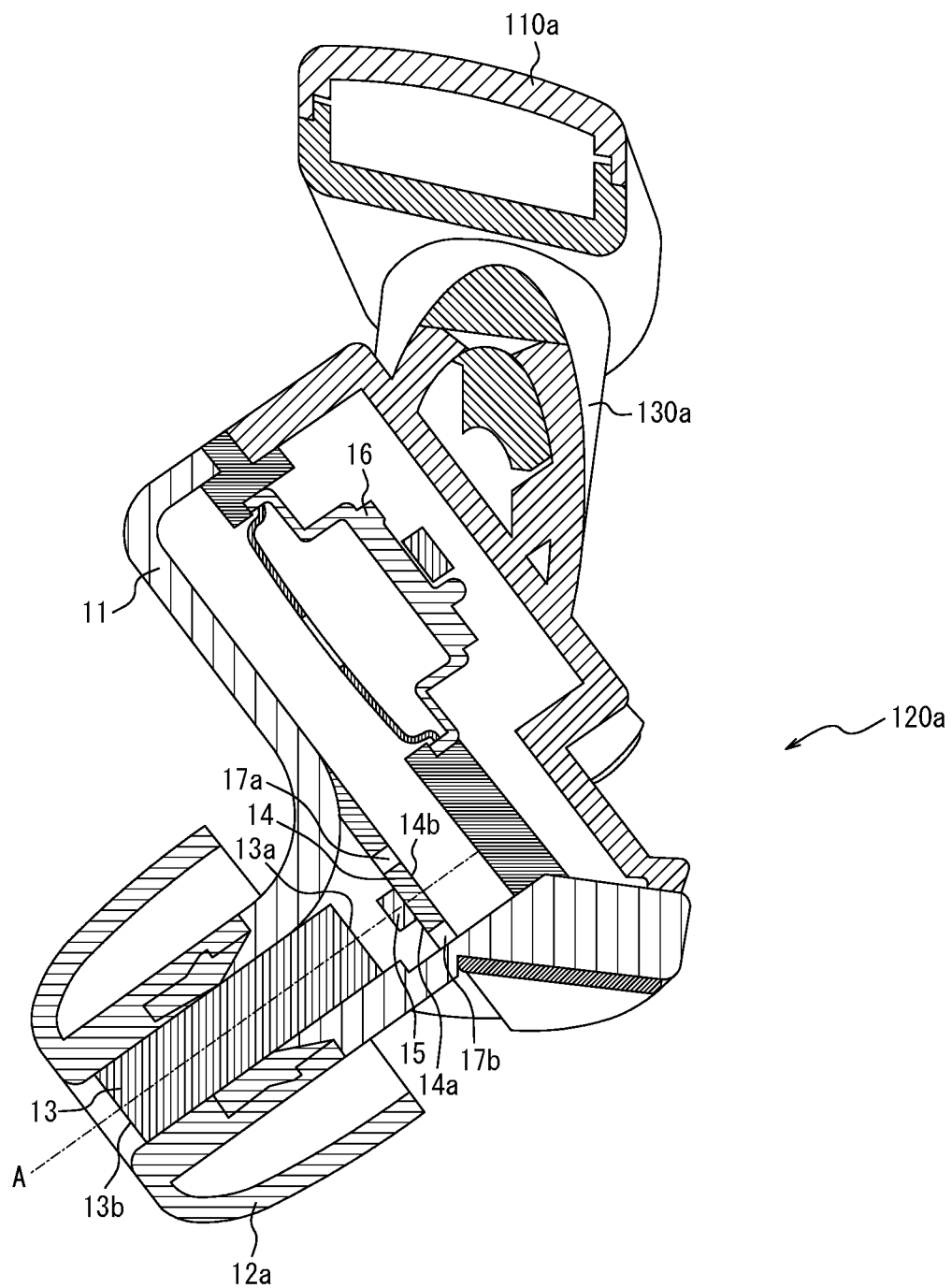
FIG. 15 is a cross-sectional view taken from line A-A of the measurement instrument in FIG. 14.

FIG. 15 is a cross-sectional view taken from line A-A of the measurement instrument 100 illustrated in FIG. 14. As illustrated in FIG. 15, the outer shape of the first measurement portion 120a is formed by coupling the holder 11 and the earpiece 12a. As viewed from the insertion direction, a cylindrical space is provided in the center of the earpiece 12a. In this space, the metal tube 13 is held. The substrate 14 is provided inside the holder 11. The measurement unit 15 is arranged on the first surface 14a of the substrate 14 at a position crossing the axis A. The substrate 14 has the first opening 17a and the second opening 17b. The sound output unit 16 is provided at a position which does not intersect the axis A. The positions of the first opening 17a and the second opening 17b on the substrate 14, and the position of the sound output 16 in the measurement apparatus 30 are determined appropriately so as to satisfy ΔD=|D1−D2|=L (n+½). Since the structure of the second measurement portion 120b may be configured symmetrically with the first measurement portion 120a, the description thereof will be omitted.

With the above configuration, the measurement instrument 100 can easily measure the body temperature of a subject wearing the measurement instrument 100 accurately, and improve the acoustic characteristics of sound to be outputted.

It has been described that, the measurement instrument 100 illustrated in FIG. 14 includes two measurement portions, namely, the first measurement portion 120a and the second measurement portion 120b. However, the measurement instrument 100 may, for example, include only one measurement portion. For example, one of the first measurement portion 120a and the second measurement portion 120b has the functions of measuring subject's body temperature and outputting sound, and the other one only has the function of outputting sound. In addition, the measurement instrument 100 may determine the subject's body temperature based on body temperature values acquired from two measurement portions, namely, the first measurement portion 120a and the second measurement portion 120b, for example, by calculating the average value of two body temperature values.

The measurement instrument 100 illustrated in FIG. 14 may be configured such that one of the first measurement portion 120a and the second measurement portion 120b is the measurement apparatus 30 according to the present embodiment, and the other one is a measurement apparatus for measuring biological information other than body temperature. For example, the other one may be configured as a blood flow measurement apparatus to be inserted in a subject's ear to measure the blood flow of the subject. The blood flow measurement apparatus may, for example, be configured to irradiate laser light to the subject and calculate the blood flow based on the reflected light of the laser light. In another example, the other one may be configured as an oxygen saturation measurement apparatus to be inserted in a subject's ear to measure the oxygen saturation of the subject. The oxygen saturation measurement apparatus may, for example, be configured to irradiate visible light and infrared light to the subject and calculate the oxygen saturation based on the ratio of the intensities of the visible light and the infrared light passing through the subject or reflected from the subject.

Embodiment 4

Next, Embodiment 4 will be described. In Embodiment 4, a smartphone 3000 is used instead of the control apparatus 500, which is used in the measurement system of Embodiment 1. In Embodiment 4, the same reference numbers are assigned to members similar to those of Embodiment 1, and description thereof will be omitted.

Figure 16:
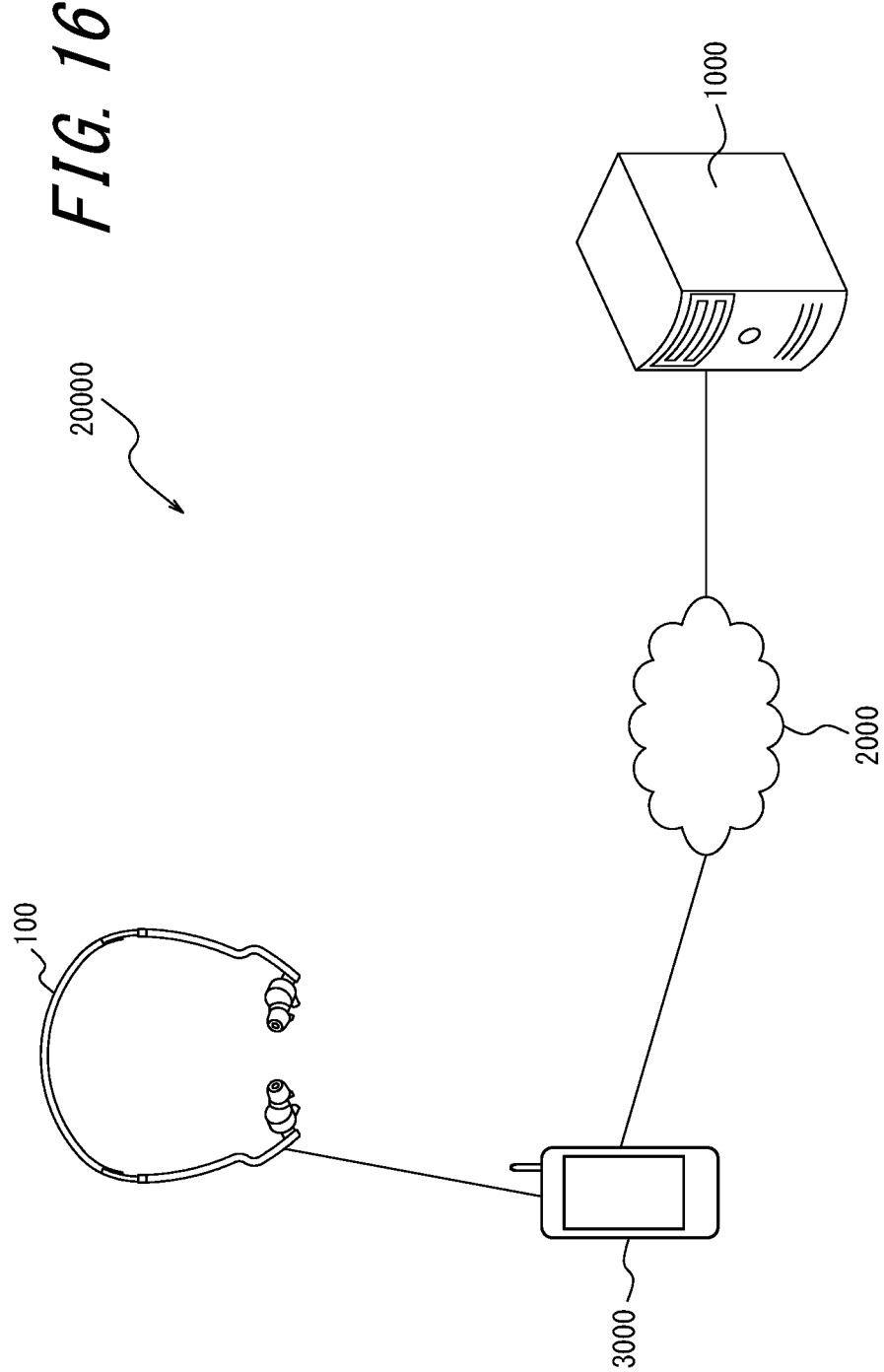
FIG. 16 illustrates a configuration example of a measurement system according to Embodiment 4.

FIG. 16 illustrates a configuration example of a measurement system 20000 according to Embodiment 4. As illustrated in FIG. 16, compared to the measurement system 10000 according to Embodiment 1, the smartphone 3000 is used instead of the control apparatus 500 is used in the measurement system 20000 according to the present embodiment. The smartphone 3000 is communicably connected to the measurement instrument 100 in a wireless manner, a wired manner, or a combination of these. In addition, the smartphone 3000 is communicably connected to the server 1000 via the network 2000.

Figure 17:
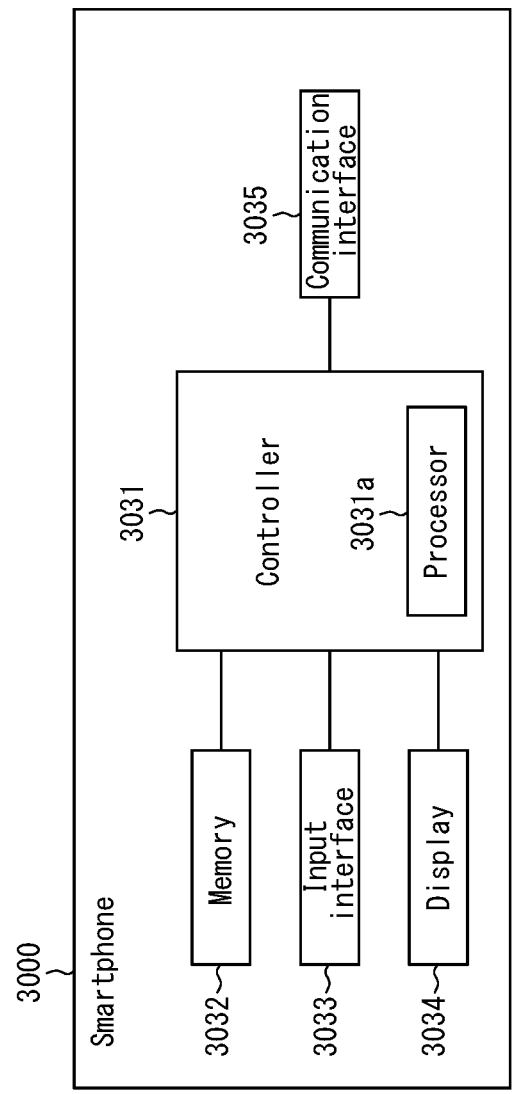
FIG. 17 illustrates an example of functional blocks provided with the smartphone in FIG. 16.

Next, an example of the functional blocks provided by the smartphone 3000 illustrated in FIG. 16 will be described with reference to FIG. 17. The smartphone 3000 includes a controller 3031, a memory 3032, an input interface 3033, a display 3034, and a communication interface 3035 as function units.

The controller 3031 includes at least one processor 3031a for controlling and managing the whole smartphone 3000, including each functional block of the smartphone 3000. The controller 3031 includes at least one processor 3031a such as a CPU configured to execute a program prescribing a control procedure, and thus enables its functions. Such a program is stored in, for example, the memory 3032 or an external storage medium connected to the smartphone 3000. As the specific configuration of the processor 3031a, those enumerated in the description of the processor 1054a can be used.

The controller 3031 may perform the same processing with the controller 1054 of the control apparatus 500 in Embodiment 1.

The memory 3032 can be constituted by a semiconductor memory, a magnetic memory, or the like. The memory 3032 stores various kinds of information, a program for operating the smartphone 3000, and the like. The memory 3032 may also function as a working memory.

The input interface 3033 is configured to receive operation input by a user of the smartphone 3000 (for example, a subject), and is constituted by, for example, operation buttons (operation keys). The input interface 3033 may also be constituted by a touchscreen, and on a part of the display device which is the display 3034, an input area may be displayed to receive touch operation input by a user.

The display 3034 is constituted by a well-known display, for example, a LCD (Liquid Crystal Display), an OELD (Organic Electro-Luminescence Display), or an IELD (Inorganic Electro-Luminescence Display).

The communication interface 3035 transmits and receives various kinds of information by communicating with the measurement instrument 100 and the server 1000. The communication interface 3035 can transmit and receive information using a network configured in a wireless manner, a wired manner, or a combination of these.

Figure 18:
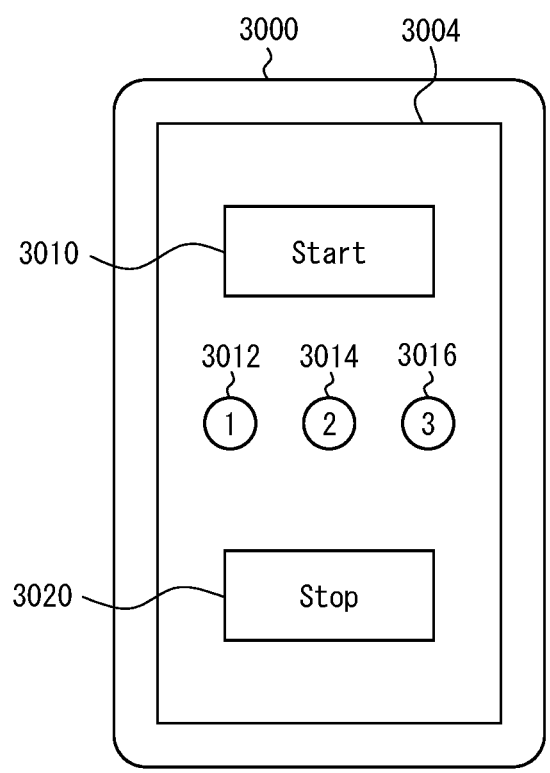
FIG. 18 is a schematic diagram illustrating a display screen of the smartphone in FIG. 16.

Next, an operation screen of the smartphone illustrated in FIG. 16 will be described with reference to FIG. 18. FIG. 18 is a schematic diagram of the operation screen of the smartphone 3000 illustrated in FIG. 16.

As illustrated in FIG. 18, a start button 3010, various functional buttons 3012, 3014 and 3016, and a stop button 3020 are displayed on the display 3034 of the smartphone 3000. The display 3034 of the smartphone 3000 is a touch panel display. When a user touches an image displayed on the display 3034 with a finger or the like, an operation input corresponding to the image is performed. For example, a subject can start measurement processing of biological information by the measurement instrument 100, by performing the operation input of selecting the start button 3010. For each of the various functional buttons 3012, 3014 and 3016, for example, a function to start predetermined processing may be set.

According to the present disclosure, by providing a function for starting predetermined processing, for example, when storing vital data at an arbitrary time point or when recording vital data continuously, it is possible to tag the data as marks for review. Also, according to the present disclosure, by provided a function for starting predetermined processing, for example, acquisition of location information and recording of surrounding scenery may also be performed at the same time. As a specific example, in the case of jogging, there are ways to use this function such as tagging at the first point of the jogging course, tagging at the second point of the jogging course, tagging at the third point of the jogging course, and the like. In another specific example, in the case of running on a bicycle, there are ways to use this function such as tagging at the first point of the cycling course, tagging at the second point of the cycling course, tagging at the third point of the cycling course, and the like.

Figure 19:
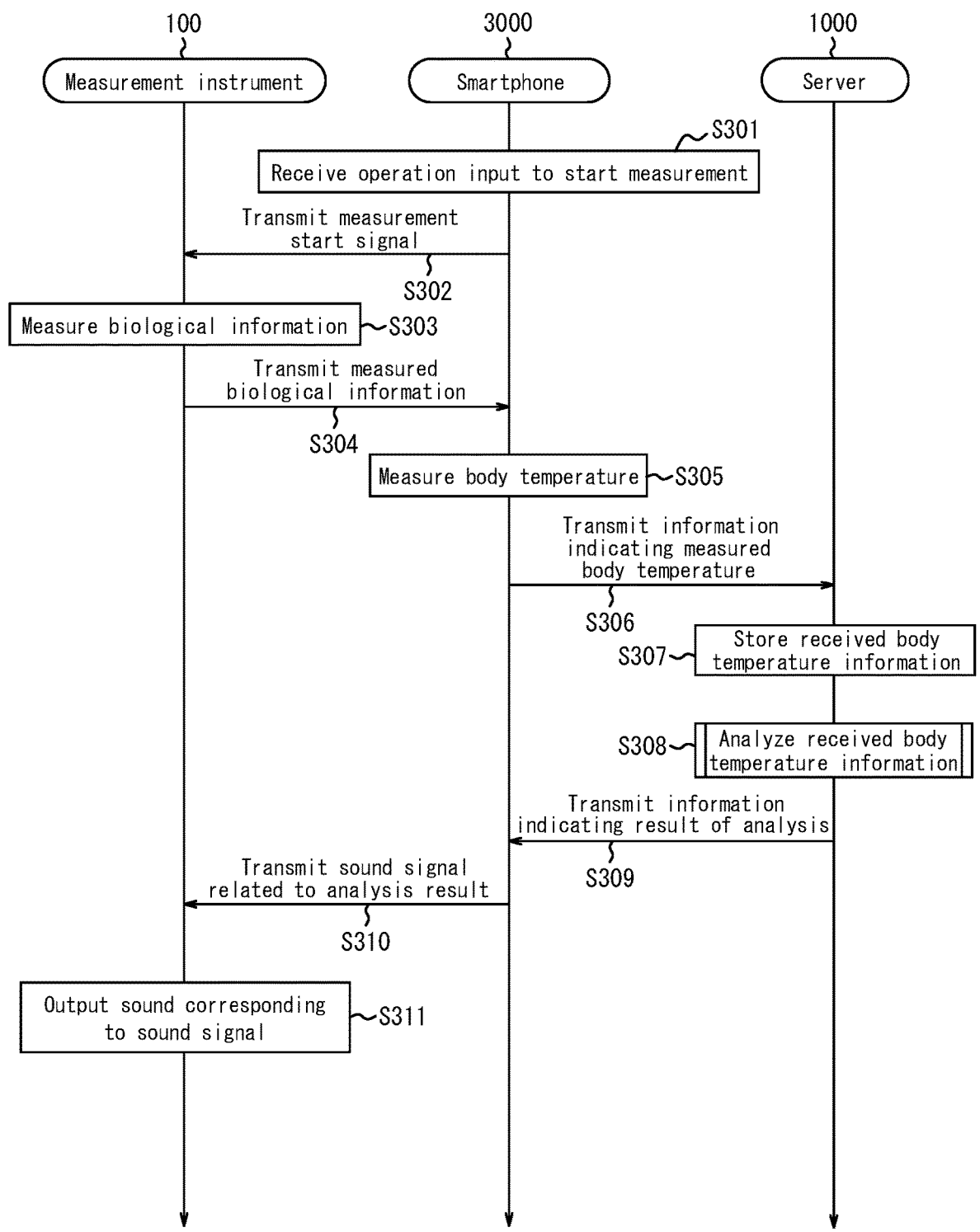
FIG. 19 is a sequence chart illustrating an example of processing performed by the measurement system in FIG. 16.

Next, an example of processing performed by the measurement system 20000 illustrated in FIG. 16 will be described with reference to FIG. 19. FIG. 19 is a sequence chart illustrating an example of processing by the measurement system 20000. The sequence illustrated in FIG. 19 may be started, for example, with a user wearing the measurement instrument 100.

Initially, the smartphone 3000 receives an operation input indicating measurement start from a subject (Step S301).

Upon receiving the operation input, the smartphone 3000 transmits a measurement start signal to the measurement instrument 100 (Step S302).

Based on the measurement start signal, the measurement instrument 100 measures biological information using the measurement unit 15 of the measurement apparatus 10 (Step S303).

Then, the measurement instrument 100 transmits the biological information measured by the measurement unit 15 to the smartphone 3000 (Step S304).

Based on the biological information acquired from the measurement instrument 100, the smartphone 3000 measures the body temperature of the subject (Step S305).

Then, the smartphone 3000 transmits information indicating the measured body temperature to the server 1000 (Step S306).

Upon receiving the body temperature information from the smartphone 3000, the server 1000 stores the received body temperature information in the memory 1003 (Step S307).

Further, the server 1000 analyzes the body temperature information received from the smartphone 3000 (Step S308).

Then, the server 1000 transmits information indicating the result of the analysis to the smartphone 3000 (Step S309).

Based on the received analysis result, the smartphone 3000 transmits a sound signal related to the analysis result to the measurement instrument 100 (Step S310).

Then, the measurement instrument 100 outputs a sound corresponding to the sound signal from the sound output unit 16 (Step S311). Through the output of the sound, the subject can be notified of the analysis result.

In Step S310, the smartphone 3000 may output a notification without transmitting the sound signal. For example, the smartphone 3000 may perform the notification by displaying the analysis result on the display 3034.

Further, for example, the controller 3031 of the smartphone 3000 may cause the display 3004 to display a list of music information stored in the memory 3032. In addition, the controller 3031 may cause the measurement instrument 100 to output music of the display list selected by a user via the input interface 3033.

However, the measurement instrument 100 according to the present disclosure is not limited to the examples described in the above embodiments. Note that the measurement instrument 100 may have various modifications including earphone type, such as a type in which on only one ear an earpiece is to be worn, and the like.

A plurality of embodiments has been described for a complete and clear disclosure. However, it is to be noted that the appended claims are not limited to the embodiments described above, and are to be construed as encompassing all of the possible modifications and alternate configurations that a person of ordinary skill in the art could make within the scope of the fundamental features illustrated in this disclosure. Moreover, each requirement described in these embodiments can be freely combined.

For example, it has been described in the above embodiments that the substrate 14 has two openings, but the number of openings provided on the substrate 14 is not necessarily two. For example, the substrate 14 may have three or more openings, resulting in a corresponding number of paths in the measurement apparatus. These openings are provided at positions on the substrate 14 such that the acoustic characteristics of sound to be inputted to the first end 13*a* of the metal tube 13 meet the target acoustic characteristics.

In Embodiment 1, it has been described that the first path and the second path are distinguished by the first opening 17*a* and the second opening 17*b* provided on the substrate 14. The first path and the second path, however, are not necessarily to be distinguished by the first opening 17*a* and the second opening 17*b* provided on the substrate 14. For example, two ducts extending from the sound output unit 16 to the first end 13*a* of the metal tube 13 may be provided, and thereby the first path and the second path are distinguished.

Further, in the above embodiments, the music data may be stored in the control apparatus 500 and the smartphone 3000, and the music may be transmitted to the measurement instrument 100 as sound information to be outputted from the measurement instrument 100, upon an operation from the control apparatus 500 or the smartphone 3000.

In addition, in each of the above embodiments, it has been assumed that, for example, the analysis of body temperature information is performed by the server 1000, however, the present disclosure is not limited to this. For example, the analysis of biological information such as body temperature information may be performed by the measurement apparatus 500 or the smartphone 3000.

The invention claimed is:

1. A measurement apparatus, comprising:
   a metal tube having a first end and a second end;
   a measurement unit which is arranged at a first end side of the metal tube and is capable of measuring electromagnetic radiation incident from the second end of the metal tube;
   a sound output unit configured to output sound; and
   a first path and a second path to the first end of the metal tube for sound outputted from the sound output unit;
   wherein
   the first path and the second path have different lengths.

2. The measurement apparatus according to claim 1, wherein a difference in length between the first path and the second path is such that an acoustic characteristic at the first end of the metal tube of sound outputted from the sound output unit is a predetermined target acoustic characteristic.

3. The measurement apparatus according to claim 1, wherein the first path, the second path, and a length from the first end to the second end of the metal tube satisfy:

$$|D1-D2|=L(n+\tfrac{1}{2}) \tag{1}$$

wherein D1 represents a length of the first path, D2 represents a length of the second path, L represents a length of the metal tube, and n is an integer greater than or equal to 0.

4. The measurement apparatus according to claim 1, further comprising a substrate which is provided between the metal tube and the sound output unit and has a first opening and a second opening; wherein
the first path is a path via the first opening; and
the second path is a path via the second opening.

5. The measurement apparatus according to claim 1, further comprising a duct forming at least one of the first path and the second path.

6. The measurement apparatus according to claim 1, wherein the electromagnetic radiation is infrared radiation.

7. The measurement apparatus according to claim 1, wherein the metal tube is a cylindrical member comprising an inner surface with high reflectance.

8. A measurement instrument, comprising:
a first measurement unit configured as a blood flow measurement apparatus capable of measuring blood flow; and
the measurement apparatus according to claim 1.

9. A measurement system, comprising:
the measurement apparatus according to claim 1;
a control apparatus for controlling operation of the measurement apparatus; and
a server connected to the measurement apparatus via a network, wherein the server is configured to receive information on electromagnetic radiation measured by the measurement apparatus, analyze the received information based on information stored in a memory, and transmit the analyzed information to the control apparatus.

10. The measurement system according to claim 9, wherein the server is configured to store at least one of an average body temperature and an individual average body temperature, and generate analyzed information based on the received information and at least one of the average body temperature and the individual average body temperature.

11. The measurement system according to claim 9, wherein a memory of the control apparatus is configured to store, as sound output information to be outputted to a measurement instrument, at least one of health information indicating a health condition, music information related to music, and environmental information around the measurement apparatus, wherein the measurement instrument comprises a first measurement unit configured as a blood flow measurement apparatus capable of measuring blood flow and the measurement apparatus according to claim 1.

12. A measurement system, comprising:
the measurement apparatus according to claim 1;
a smartphone configured to control operation of the measurement apparatus; and
a server connected to the measurement apparatus via a network, wherein the server is configured to receive information on electromagnetic radiation measured by the measurement apparatus, analyze the received information based on information stored in a memory, and transmit analysis information indicating a result of the analysis to the control apparatus.

13. A server connected to a control apparatus for controlling operation of the measurement apparatus according to claim 1 via a network; wherein the server is configured to
receive information on electromagnetic radiation measured by the measurement apparatus,
analyze the received information based on information stored in a memory, and
transmit analysis information indicating a result of the analysis to the control apparatus.

14. An analysis method performed by a server connected to a control apparatus configured to control operation of a measurement apparatus via a network, said analysis method comprising:
receiving information on electromagnetic radiation measured by the measurement apparatus;
analyzing the received information based on information stored in a memory; and
transmitting analysis information indicating a result of the analysis to the control apparatus,
wherein the measurement apparatus includes:
a metal tube having a first end and a second end;
a measurement unit which is arranged at a first end side of the metal tube and is capable of measuring the electromagnetic radiation incident from the second end of the metal tube;
a sound output unit configured to output sound; and
a first path and a second path to the first end of the metal tube for the sound outputted from the sound output unit, wherein the first path and the second path have different lengths.

15. A non-transitory computer readable storage medium storing an analysis program which, when executed by a computer, causes the computer to:
receive information on electromagnetic radiation measured by a measurement apparatus;
analyze the received information based on information stored in a memory; and
transmit analysis information indicating a result of the analysis to a control apparatus,
wherein the measurement apparatus includes:
a metal tube having a first end and a second end;
a measurement unit which is arranged at a first end side of the metal tube and is capable of measuring the electromagnetic radiation incident from the second end of the metal tube;
a sound output unit configured to output sound; and
a first path and a second path to the first end of the metal tube for the sound outputted from the sound output unit, wherein the first path and the second path have different lengths.

16. A data structure configured for use in a computer, comprising:
information on electromagnetic radiation measured by the measurement apparatus according to claim 1:
a user ID of a user of the measurement apparatus:
an average body temperature of a group to which the user belongs; and
an individual average body temperature of the user; wherein
the computer is used to determine whether information on electromagnetic radiation measured by the measurement apparatus is abnormal based on at least one of the average body temperature and the individual average body temperature.

* * * * *